United States Patent
Jin et al.

(10) Patent No.: US 10,584,410 B2
(45) Date of Patent: Mar. 10, 2020

(54) MULTI-ELECTRODE MOLECULAR SENSING DEVICES AND METHODS OF MAKING THE SAME

(71) Applicant: Roswell Biotechnologies, Inc., San Diego, CA (US)

(72) Inventors: Sungho Jin, San Diego, CA (US); Barry L. Merriman, San Diego, CA (US); Tim Geiser, Petaluma, CA (US); Chulmin Choi, San Diego, CA (US); Paul Mola, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

(21) Appl. No.: 15/979,135

(22) Filed: May 14, 2018

(65) Prior Publication Data

US 2018/0259474 A1    Sep. 13, 2018

Related U.S. Application Data

(60) Division of application No. 15/796,080, filed on Oct. 27, 2017, now Pat. No. 10,151,722, which is a
(Continued)

(51) Int. Cl.
*C23C 16/01* (2006.01)
*G01N 27/02* (2006.01)
(Continued)

(52) U.S. Cl.
CPC .............. *C23C 16/01* (2013.01); *G01N 27/04* (2013.01); *G01N 27/221* (2013.01); *G01N 27/4145* (2013.01)

(58) Field of Classification Search
CPC ........ C23C 16/01; G01N 27/02; G01N 27/04; G01N 27/22
(Continued)

(56) References Cited

U.S. PATENT DOCUMENTS 5,082,627 A    1/1992    Stanbro
5,194,133 A    3/1993    Clark et al.
(Continued)

FOREIGN PATENT DOCUMENTS

CN    104685066    6/2015
CN    104703700    6/2015
(Continued)

OTHER PUBLICATIONS

Mastrototaro, J. J. et al, IEEE Engineering in Medicine & Biology Society 11th Annual International Conference 1989, 1 page.*
(Continued)

*Primary Examiner* — Arlen Soderquist
(74) *Attorney, Agent, or Firm* — Snell & Wilmer, L.L.P.

(57) ABSTRACT

A molecular sensor includes a substrate defining a substrate plane, and a plurality of pairs of electrode sheets above or below the substrate at an angle to the substrate plane. The molecular sensor further includes a plurality of inner dielectric sheets between each electrode sheet in each pair of electrode sheets of the plurality of pairs, and an outer dielectric sheet between each pair of electrode sheets of the plurality of pairs.

18 Claims, 23 Drawing Sheets

Related U.S. Application Data continuation of application No. 15/220,307, filed on Jul. 26, 2016, now Pat. No. 9,829,456.

(51) Int. Cl.
  *G01N 27/04* (2006.01)
  *G01N 27/22* (2006.01)
  *G01N 27/414* (2006.01)

(58) Field of Classification Search
  USPC ....... 422/82.01–82.04; 436/86, 94, 149–151, 436/512, 518, 527; 427/97.1, 98.4, 427/117–118, 123–126.6, 97.3–97.4
  See application file for complete search history.

(56) References Cited

U.S. PATENT DOCUMENTS

| | | | |
|---|---|---|---|
| 5,366,140 A | 11/1994 | Koskenmaki et al. | |
| 5,414,588 A | 5/1995 | Barbee, Jr. | |
| 5,486,449 A | 1/1996 | Honso et al. | |
| 5,532,128 A | 7/1996 | Eggers et al. | |
| 5,583,359 A | 12/1996 | Ng et al. | |
| 5,639,507 A | 6/1997 | Galvagni et al. | |
| 5,767,687 A * | 6/1998 | Geist | G01N 27/221 324/663 |
| 5,871,918 A | 2/1999 | Thorp et al. | |
| 5,881,184 A | 3/1999 | Guidash | |
| 5,982,018 A | 11/1999 | Wark | |
| 6,051,380 A | 4/2000 | Sosnowski et al. | |
| 6,060,023 A | 5/2000 | Maracas | |
| 6,094,335 A | 7/2000 | Early | |
| 6,110,354 A | 8/2000 | Saban | |
| 6,123,819 A | 9/2000 | Peeters | |
| 6,144,023 A | 11/2000 | Clerc | |
| 6,238,927 B1 | 5/2001 | Abrams et al. | |
| 6,440,662 B1 | 8/2002 | Gerwen et al. | |
| 6,464,889 B1 | 10/2002 | Lee et al. | |
| 6,506,564 B1 | 1/2003 | Mirkin et al. | |
| 6,537,747 B1 | 3/2003 | Mills, Jr. et al. | |
| 6,670,131 B2 | 12/2003 | Hashimoto | |
| 6,673,533 B1 | 1/2004 | Wohlstadter et al. | |
| 6,716,620 B2 | 4/2004 | Bashir et al. | |
| 6,749,731 B2 | 6/2004 | Kobori | |
| 6,762,050 B2 * | 7/2004 | Fukushima | B41J 2/01 422/82.01 |
| 6,764,745 B1 | 7/2004 | Karasawa et al. | |
| 6,790,341 B1 | 9/2004 | Saban | |
| 6,824,974 B2 * | 11/2004 | Pisharody | C12Q 1/003 205/777.5 |
| 6,861,224 B2 | 3/2005 | Fujita et al. | |
| 6,916,614 B1 | 7/2005 | Takenaka et al. | |
| 6,958,216 B2 | 10/2005 | Kelley | |
| 7,015,046 B2 * | 3/2006 | Wohlstadter | B01L 3/5027 204/291 |
| 7,075,428 B1 * | 7/2006 | Oleynik | G01N 33/54373 340/539.26 |
| 7,169,272 B2 | 1/2007 | Fritsch et al. | |
| 7,183,055 B2 | 2/2007 | Van Der Weide | |
| 7,189,435 B2 | 3/2007 | Tuominen et al. | |
| 7,202,480 B2 | 4/2007 | Yokoi et al. | |
| 7,208,077 B1 * | 4/2007 | Albers | G01N 27/3277 204/403.01 |
| 7,258,731 B2 | 8/2007 | D'Urso et al. | |
| 7,276,206 B2 | 10/2007 | Augustine et al. | |
| 7,399,585 B2 | 7/2008 | Gau | |
| 7,432,120 B2 * | 10/2008 | Mascolo | H01L 21/0337 257/E21.038 |
| 7,470,533 B2 | 12/2008 | Xu et al. | |
| 7,507,320 B2 | 3/2009 | Hwang et al. | |
| 7,531,120 B2 | 5/2009 | Van Rijn et al. | |
| 7,579,823 B1 | 8/2009 | Ayliffe | |
| 7,691,433 B2 | 4/2010 | Kronholz et al. | |
| 7,785,785 B2 | 8/2010 | Pourmand et al. | |
| 7,834,344 B2 * | 11/2010 | Mascolo | H01L 51/0021 257/28 |
| 7,851,045 B2 | 12/2010 | Gandon et al. | |
| 7,886,601 B2 * | 2/2011 | Merassi | G01P 1/023 361/280 |
| 7,901,629 B2 * | 3/2011 | Calatzis | G01N 27/07 422/536 |
| 7,943,394 B2 | 5/2011 | Flandre et al. | |
| 8,241,508 B2 | 8/2012 | D'Urso | |
| 8,351,181 B1 | 1/2013 | Ahn | |
| 8,591,816 B2 | 11/2013 | Calatzis et al. | |
| 8,652,768 B1 | 2/2014 | Huber et al. | |
| 8,753,893 B2 | 6/2014 | Liu et al. | |
| 8,927,464 B2 | 1/2015 | Aizenberg et al. | |
| 8,940,663 B2 | 1/2015 | Iqbal et al. | |
| 9,108,880 B2 | 8/2015 | Jin et al. | |
| 9,306,164 B1 * | 4/2016 | Chang | H01L 21/76816 |
| 9,829,456 B1 | 11/2017 | Merriman et al. | |
| 9,956,743 B2 | 5/2018 | Jin et al. | |
| 10,036,064 B2 | 7/2018 | Merriman et al. | |
| 10,125,420 B2 | 11/2018 | Jin et al. | |
| 10,151,722 B2 | 12/2018 | Jin et al. | |
| 10,508,296 B2 | 12/2019 | Merriman et al. | |
| 10,526,696 B2 | 1/2020 | Jin et al. | |
| 2002/0022223 A1 | 2/2002 | Connolly | |
| 2002/0090649 A1 * | 7/2002 | Chan | B01J 19/0046 435/7.1 |
| 2002/0137083 A1 | 9/2002 | Kobori et al. | |
| 2002/0138049 A1 | 9/2002 | Allen et al. | |
| 2002/0142150 A1 | 10/2002 | Baumann et al. | |
| 2002/0142477 A1 * | 10/2002 | Lewis | G01N 33/0031 436/151 |
| 2002/0172963 A1 | 11/2002 | Kelley et al. | |
| 2002/0184939 A1 | 12/2002 | Yadav | |
| 2003/0025133 A1 | 2/2003 | Brousseau | |
| 2003/0040100 A1 | 2/2003 | Connolly et al. | |
| 2003/0064390 A1 | 4/2003 | Schülein et al. | |
| 2003/0087296 A1 * | 5/2003 | Fujita | G01N 33/53 435/6.1 |
| 2003/0186263 A1 | 10/2003 | Frey et al. | |
| 2003/0224387 A1 * | 12/2003 | Kunwar | B82Y 15/00 435/6.11 |
| 2004/0014106 A1 | 1/2004 | Patno et al. | |
| 2004/0023253 A1 | 2/2004 | Kunwar et al. | |
| 2004/0038090 A1 | 2/2004 | Faris | |
| 2004/0063100 A1 | 4/2004 | Wang | |
| 2004/0086929 A1 | 5/2004 | Weide et al. | |
| 2004/0096866 A1 | 5/2004 | Hoffman et al. | |
| 2004/0012161 A1 | 6/2004 | Chiu | |
| 2004/0146863 A1 * | 7/2004 | Pisharody | C12Q 1/003 435/6.11 |
| 2004/0209355 A1 | 10/2004 | Edman et al. | |
| 2004/0209435 A1 * | 10/2004 | Partridge | B81C 1/00063 438/381 |
| 2004/0235016 A1 | 11/2004 | Hamers | |
| 2004/0248282 A1 | 12/2004 | Sobha | |
| 2005/0029227 A1 | 2/2005 | Chapman | |
| 2005/0067086 A1 | 3/2005 | Ito et al. | |
| 2005/0151541 A1 * | 7/2005 | Brinz | G01N 27/4162 324/438 |
| 2005/0172199 A1 | 8/2005 | Miller et al. | |
| 2005/0181195 A1 | 8/2005 | Dubrow | |
| 2005/0221473 A1 * | 10/2005 | Dubin | B82Y 30/00 435/287.2 |
| 2005/0227373 A1 * | 10/2005 | Flandre | G01N 27/221 436/518 |
| 2005/0247573 A1 | 11/2005 | Nakamura et al. | |
| 2005/0285275 A1 | 12/2005 | Son | |
| 2005/0287589 A1 | 12/2005 | Connolly | |
| 2006/0003482 A1 | 1/2006 | Chinthakindi et al. | |
| 2006/0019273 A1 | 1/2006 | Connolly et al. | |
| 2006/0024504 A1 | 2/2006 | Nelson et al. | |
| 2006/0024508 A1 | 2/2006 | D'Urso et al. | |
| 2006/0029808 A1 | 2/2006 | Zhai et al. | |
| 2006/0051919 A1 * | 3/2006 | Mascolo | H01L 51/0021 438/253 |
| 2006/0051946 A1 * | 3/2006 | Mascolo | H01L 21/0337 438/596 |

(56) References Cited

U.S. PATENT DOCUMENTS

| | | | |
|---|---|---|---|
| 2006/0105449 A1* | 5/2006 | Larmer | B01L 3/5085 435/287.2 |
| 2006/0105467 A1* | 5/2006 | Niksa | G01N 27/126 436/150 |
| 2006/0128239 A1 | 5/2006 | Nun et al. | |
| 2006/0147983 A1 | 7/2006 | O'uchi | |
| 2006/0154489 A1 | 7/2006 | Tornow | |
| 2006/0275853 A1* | 12/2006 | Mathew | G01N 27/3276 435/7.93 |
| 2007/0026193 A1 | 2/2007 | Luzinov et al. | |
| 2007/0048748 A1 | 3/2007 | Williams et al. | |
| 2007/0140902 A1* | 6/2007 | Calatzis | G01N 27/07 422/400 |
| 2007/0148815 A1 | 6/2007 | Chao et al. | |
| 2007/0184247 A1 | 9/2007 | Simpson et al. | |
| 2007/0207487 A1 | 9/2007 | Emig et al. | |
| 2007/0231542 A1 | 10/2007 | Deng | |
| 2008/0098815 A1* | 5/2008 | Merassi | G01P 1/023 73/514.18 |
| 2008/0199657 A1 | 8/2008 | Capron et al. | |
| 2008/0199659 A1 | 8/2008 | Zhao | |
| 2009/0011222 A1 | 1/2009 | Xiu et al. | |
| 2009/0017571 A1 | 1/2009 | Nuckolls | |
| 2009/0020428 A1 | 1/2009 | Levitan | |
| 2009/0062684 A1* | 3/2009 | Gregersen | A61B 5/02007 600/547 |
| 2009/0152109 A1 | 6/2009 | Whitehead et al. | |
| 2009/0170716 A1 | 7/2009 | Su et al. | |
| 2009/0178935 A1* | 7/2009 | Reymond | G01N 27/3273 205/777.5 |
| 2009/0295372 A1 | 12/2009 | Krstic et al. | |
| 2009/0297913 A1 | 12/2009 | Zhang et al. | |
| 2009/0324308 A1 | 12/2009 | Law et al. | |
| 2010/0038342 A1 | 2/2010 | Lim et al. | |
| 2010/0044212 A1 | 2/2010 | Kim et al. | |
| 2010/0055397 A1 | 3/2010 | Kurihara et al. | |
| 2010/0132771 A1 | 6/2010 | Lu | |
| 2010/0142259 A1 | 6/2010 | Drndic et al. | |
| 2010/0149530 A1 | 6/2010 | Tomaru | |
| 2010/0184062 A1 | 7/2010 | Steinmueller-Nethl et al. | |
| 2010/0188109 A1 | 7/2010 | Edel et al. | |
| 2010/0194409 A1 | 8/2010 | Gao et al. | |
| 2010/0206367 A1 | 8/2010 | Jeong et al. | |
| 2010/0280397 A1* | 11/2010 | Feldman | A61B 5/0535 600/486 |
| 2010/0285275 A1 | 11/2010 | Baca et al. | |
| 2010/0285601 A1 | 11/2010 | Kong et al. | |
| 2010/0288543 A1 | 11/2010 | Hung et al. | |
| 2010/0300899 A1 | 12/2010 | Levine et al. | |
| 2011/0056845 A1 | 3/2011 | Stellacci et al. | |
| 2011/0076783 A1 | 3/2011 | Liu et al. | |
| 2011/0091787 A1 | 4/2011 | McGrath et al. | |
| 2011/0160077 A1 | 6/2011 | Chaisson et al. | |
| 2011/0166034 A1 | 7/2011 | Kwong et al. | |
| 2011/0217763 A1 | 9/2011 | Rasooly et al. | |
| 2011/0227558 A1 | 9/2011 | Mannion et al. | |
| 2011/0229667 A1 | 9/2011 | Jin et al. | |
| 2011/0233075 A1 | 9/2011 | Soleymani et al. | |
| 2011/0287956 A1 | 11/2011 | Iqbal et al. | |
| 2011/0291673 A1 | 12/2011 | Shibata et al. | |
| 2011/0311853 A1* | 12/2011 | Fratti | H01M 2/1022 429/100 |
| 2011/0312529 A1 | 12/2011 | He et al. | |
| 2012/0060905 A1 | 3/2012 | Fogel et al. | |
| 2012/0220046 A1 | 8/2012 | Chao | |
| 2012/0258870 A1 | 10/2012 | Schwartz et al. | |
| 2012/0286332 A1 | 11/2012 | Rothberg et al. | |
| 2013/0049158 A1 | 2/2013 | Hong et al. | |
| 2013/0108956 A1 | 5/2013 | Lu et al. | |
| 2013/0109577 A1 | 5/2013 | Korlach et al. | |
| 2013/0162276 A1 | 6/2013 | Lee et al. | |
| 2013/0183492 A1 | 7/2013 | Lee et al. | |
| 2013/0214875 A1 | 8/2013 | Duncan et al. | |
| 2013/0239349 A1 | 9/2013 | Knights et al. | |
| 2013/0245416 A1 | 9/2013 | Yarmush et al. | |
| 2013/0273340 A1 | 10/2013 | Neretina et al. | |
| 2013/0281325 A1 | 10/2013 | Elibol et al. | |
| 2013/0331299 A1 | 12/2013 | Reda et al. | |
| 2014/0001055 A1 | 1/2014 | Elibol et al. | |
| 2014/0011013 A1 | 1/2014 | Jin | |
| 2014/0018262 A1 | 1/2014 | Reda et al. | |
| 2014/0027775 A1 | 1/2014 | Quick et al. | |
| 2014/0048776 A1 | 2/2014 | Huang et al. | |
| 2014/0057283 A1* | 2/2014 | Wang | C12M 23/12 435/7.2 |
| 2014/0061049 A1* | 3/2014 | Lo | G01N 27/44704 204/547 |
| 2014/0079592 A1 | 3/2014 | Chang et al. | |
| 2014/0170567 A1 | 6/2014 | Sakamoto et al. | |
| 2014/0174927 A1 | 6/2014 | Bashir et al. | |
| 2014/0197459 A1 | 7/2014 | Kis et al. | |
| 2014/0218637 A1 | 8/2014 | Gao et al. | |
| 2014/0235493 A1* | 8/2014 | Zang | G01N 27/127 506/9 |
| 2014/0253827 A1 | 9/2014 | Gao et al. | |
| 2014/0284667 A1* | 9/2014 | Basker | H01L 29/6681 257/288 |
| 2014/0367749 A1 | 12/2014 | Bai et al. | |
| 2015/0005188 A1 | 1/2015 | Levner et al. | |
| 2015/0017655 A1 | 1/2015 | Huang et al. | |
| 2015/0049332 A1 | 2/2015 | Sun et al. | |
| 2015/0057182 A1 | 2/2015 | Merriman et al. | |
| 2015/0068892 A1 | 3/2015 | Ueno et al. | |
| 2015/0148264 A1* | 5/2015 | Esfandyarpour | C12Q 1/6853 506/38 |
| 2015/0177150 A1 | 6/2015 | Rothberg et al. | |
| 2015/0191709 A1 | 7/2015 | Heron et al. | |
| 2015/0263203 A1 | 9/2015 | Lewis et al. | |
| 2015/0293025 A1 | 10/2015 | Ninomiya et al. | |
| 2015/0294875 A1 | 10/2015 | Khondaker et al. | |
| 2015/0344945 A1 | 12/2015 | Mandell et al. | |
| 2016/0017416 A1 | 1/2016 | Boyanov et al. | |
| 2016/0045378 A1* | 2/2016 | Geloen | A61F 13/42 604/361 |
| 2016/0155971 A1 | 6/2016 | Strachan et al. | |
| 2016/0187282 A1 | 6/2016 | Gardner et al. | |
| 2016/0284811 A1 | 9/2016 | Yu et al. | |
| 2016/0319342 A1 | 11/2016 | Kawai et al. | |
| 2016/0377564 A1* | 12/2016 | Carmignani | G01N 27/128 324/705 |
| 2017/0023512 A1 | 1/2017 | Cummins et al. | |
| 2017/0037462 A1 | 2/2017 | Turner et al. | |
| 2017/0043355 A1 | 2/2017 | Fischer | |
| 2017/0044605 A1 | 2/2017 | Merriman | |
| 2017/0131237 A1 | 5/2017 | Ikeda | |
| 2017/0184542 A1 | 6/2017 | Chatelier et al. | |
| 2017/0234825 A1 | 8/2017 | Elibol et al. | |
| 2017/0240962 A1 | 8/2017 | Merriman | |
| 2017/0332918 A1* | 11/2017 | Keane | A61B 5/02007 |
| 2018/0014786 A1* | 1/2018 | Keane | A61B 5/0422 |
| 2018/0031508 A1 | 2/2018 | Jin | |
| 2018/0031509 A1 | 2/2018 | Jin | |
| 2018/0045665 A1 | 2/2018 | Jin | |
| 2018/0297321 A1 | 10/2018 | Jin et al. | |
| 2018/0305727 A1 | 10/2018 | Merriman | |
| 2018/0340220 A1 | 11/2018 | Merriman | |
| 2019/0004003 A1 | 1/2019 | Merriman | |
| 2019/0033244 A1 | 1/2019 | Jin | |
| 2019/0039065 A1 | 2/2019 | Choi | |
| 2019/0041355 A1 | 2/2019 | Merriman | |
| 2019/0041378 A1 | 2/2019 | Choi | |
| 2019/0094175 A1 | 3/2019 | Merriman | |
| 2019/0194801 A1 | 6/2019 | Jin et al. | |
| 2019/0355442 A1 | 11/2019 | Merriman et al. | |
| 2019/0376925 A1 | 12/2019 | Choi et al. | |
| 2019/0383770 A1 | 12/2019 | Choi et al. | |

FOREIGN PATENT DOCUMENTS

| | | |
|---|---|---|
| DE | 102013012145 | 1/2015 |
| EP | 2053383 | 4/2009 |
| JP | 2018-522236 | 8/2018 |

(56) References Cited

FOREIGN PATENT DOCUMENTS

| | | |
|---|---|---|
| KR | 20070059880 | 6/2007 |
| KR | 20110104245 | 9/2011 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2010022107 | 2/2010 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100637 | 6/2016 |
| WO | 2016196755 | 12/2016 |
| WO | 2016210386 | 12/2016 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | WO 2017/132567 * | 8/2017 |
| WO | WO 2017/139493 * | 8/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |

OTHER PUBLICATIONS

Mastrototaro, J. J. et al, IEEE Transactions on Biomedical Engineering 1992, 39, 271-279.*
Van Gerwin, P. et al, Sensors and Actuators B 1998, 49, 73-80.*
Santschi, Ch. et al, Nanotechnology 2006, 17, 2722-2729.*
Javey, A. et al, Nano Letters 2007, 7, 773-777.*
Fan, Y. et al, Journal of the American Chemical Society 2007, 129, 5437-5443.*
Kitsara, M. et al, Sensors and Actuators B 2007, 127, 186-192.*
Xu, Q. et al, ACS Nano 2007, 1, 215-227.*
Berdat, D. et al, Lab on a Chip 2008, 8, 302-308.*
Dickey, M. D. et al, Nano Letters 2008, 8, 4568-4573.*
Singh, K. V. et al, Analytical and Bioanalytical Chemistry 2010, 397, 1493-1502.*
Bhura, D. K., Masters Thesis 2011, 68 pages.*
Ino, K. et al, Lab on a Chip 2011, 11, 385-388.*
Bonilla, D. et al, Analytical Chemistry 2011, 83, 1726-1731.*
Ahn, J. et al, Biosensors and Bioelectronics 2011, 26, 4690-4696.*
Singh, K. V. et al, 11th IEEE International Conference on Nanotechnology 2011, 707-710.*
Singh, K. V. et al, Langmuir 2011, 27, 13931-13939.*
Chen, X. et al, Sensors and Actuators A 2012, 175.73-77.*
Branagan, S. P. et al, Journal of the American Chemical Society 2012, 134, 8617-8624.*
Ino, K. et al, Angew.andte Chemie Ineternational Edition 2012, 51, 6648-6652.*
Botsialas, A. et al, Sensors and Actuators B 2013, 177, 776-784.*
Sanguino, P. et al, IEEE Sensors Journal 2014, 14, 1260-1265.*
Van Megan, M. J. J. et al, Key Engineering Materials 2014, 605, 107-110.*
MacNaughton, S. et al, PLOS One 2014, 9, e111377, 7 pages.*
Kitsara, M. et al, SPIE 2015, 9518, 95180Z, 9 pages.*
Alayo, N. et al, Microchim Acta 2016, 183, 1633-1639.*
Han, D. et al, Journal of Physical Chemistry C 2016, 120, 20634-20641.*
Cosofret, V. V. et al, Analytical Chemistry 1995, 67, 1647-1653.*
Henry, C. S. et al, Journal of The Electrochemical Society 1999, 146, 3367-3373.*
Briglin, S. M. et al, Sensors and Actuators B 2002, 82, 54-74.*
Lin, Z. et al, Analytical Chemistry 2008, 80, 6830-6833.*
USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
USPTO; Requirement for Restriction dated Jan. 17, 2017 in U.S. Appl. No. 15/336,557.
USPTO; Advisory Action dated Mar. 14, 2017 in U.S. Appl. No. 15/050,270.
USPTO; Non-Final Office Action dated May 16, 2017 in U.S. Appl. No. 15/336,557.
USPTO; Final Office Action dated Dec. 30, 2016 in U.S. Appl. No. 15/050,270.
USPTO; Non-Final Office Action dated Sep. 29, 2017 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Non-Final Office Action dated Feb. 9, 2018 in U.S. Appl. No. 15/728,400.
USPTO; Non-Final Office Action dated Feb. 23, 2018 in U.S. Appl. No. 15/728,412.
USPTO; Non-Final Office Action dated Feb. 23, 2018 in U.S. Appl. No. 15/796,080.
USPTO; Final Office Action dated Mar. 8, 2018 in U.S. Appl. No. 15/336,557.
PCT; International Search Report and Written Opinion dated Apr. 8, 2010 in Application No. PCT/US2009/054235.
PCT; International Search Report and Written Opinion dated Nov. 29, 2012 in Application No. PCT/US2011/001995.
PCT; International Search Report and Written Opinion dated Sep. 27, 2016 in Application No. PCT/US2016/039446.
PCT; International Search Report and Written Opinion dated May 25, 2017 in Application No. PCT/US2017/18950.
PCT; International Search Report and Written Opinion dated Jul. 26, 2017 in Application No. PCT/US2017/017231.
PCT; International Search Report and Written Opinion dated Apr. 18, 2017 in Application No. PCT/US2016/068922.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.

(56) References Cited

OTHER PUBLICATIONS

PCT; International Search Report and Written Opinion dated Apr. 13, 2018 in Application No. PCT/US2018/013140.
Fink et al. "Electrical Conduction Through DNA Molecules", Nature, vol. 398, pp. 407-410 (Jan. 20, 1999).
Stenning, "The Investigation of Grain Boundary Development and Crystal Synthesis of Thin Gold Films on Silicon Wafers,"http://www.ucl.ac.uk/~ucapikr/projects, (Mar. 31, 2009).
Bechelany et al. "Synthesis Mechanisms of Organized Nanoparticles: Influence of Annealing Temperature and Atmosphere," Crystal Growth and Design, vol. 10, pp. 587-596, (Oct. 21, 2010).
H. Nishida, et al. Self-Oriented Immobilization of DNA Polymerase Tagged by Titanium-Binding Peptide Motif, Langmuir, vol. 31, pp. 732-740, (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989).
Park, S.J. et al., "Array-Based Electrical Detection of DNA with Nanoparticle Probes," Science, vol. 295, pp. 1503-1506, (Feb. 22, 2002).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003).
Choi Y.S. et al., "Hybridization by an Electroatomical Genome on Detection on Using an Indicator-Free DNA on a Microelectrode-array DNA Chip" Bulletin of the Korean Chemistry Society, vol. 26, pp. 379-383, (2005).
Park, C.W. et al., "Fabrication of Poly-Si/ AU Nano -gaps Using Atomic-layer-deposited $Al_2O_3$ as a Sacrificial Layer," Nanotechnology, vol. 16, pp. 361-364, (Feb. 1, 2005).
Ruttkowski, E. et al., "CMOS based Arrays of Nanogaps Devices for Molecular Devices" Proceedings of 2005 5th IEEE Conference on Nanotechnology, vol. 1, pp. 438-441, (Jul. 2005).
Stagni, C. et al., "CMOS DNA Sensor Array with Integrated A/D Conversation Based on Label-Free Capacitance Measurement" IEEE Journal of Solid-State Circuits, vol. 41, pp. 2956-2964, (Nov. 20, 2006).
Schrott, W. et al., "Metal Electrodes in Plastic Microfluidic Systems" Microelectronic Engineering, vol. 86, pp. 1340-1342, (Jun. 2009).
Roy, S. et al., "Mass-Produced Nanogap Sensor Arrays for Ultra-Sensitive Detection of DNA" Journal of the American Chemical Society, vol. 131, pp. 12211-12217, (Aug. 5, 2009).
Choi, J. E. et al., "Fabrication of Microchannel with 60 Electrodes and Resistance Measurement" Flow Measurement and Instrumentation, vol. 21, pp. 178-183, (Sep. 2010).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Chen, X. et al., "Electrical Nanogap Devices for Biosensing," Materials Today, vol. 13, pp. 28-41, (Nov. 2010).
Ghindilis, A. et al., "Real Time Biosensor Platforms Fully Integrated Device for Impedimetric Assays," ECS Transactions, vol. 33, pp. 59-68, (2010).
Su, Y., "Modeling and Characteristic Study of Thin Film Based Biosensor Based on COMSOL," Mathematical Problems in Engineering, Article 581063 (6 Pages), (Apr. 7, 2014).
Blossey, R., "Self-Cleaning Surfaces-Virtual Realities," Nature Materials, vol. 2(5), pp. 301-306, (May, 2006).
Cassie, A.B.D. et al., "Wettability of Porous Surfaces," Transitions of the Faraday Society, vol. 40, pp. 546-551, (Jan. 1944) (Abstract only).
Choi, C. et al., "Strongly Superhydrophobic Silicon Nanowires by Supercritical CO2 Drying," Electronic Materials Letters, vol. 6 (2), pp. 59-64, (Jun. 2010).

Coulson S.R. et al., "Super-Repellent Composite Fluoropolymer Surfaces," The Journal of Physical Chemistry B., vol. 104(37), pp. 8836-8840, (Aug. 2000).
Gapin, A.I. et al., "CoPt Patterned Media in Anodized Aluminum Oxide Templates," Journal of Applied Physics, vol. 99(8), pp. 08G902 (1-3), (Apr. 2006).
Parkin, I. P. et al., "Self-Cleaning Coatings," Journal of Materials Chemistry, vol. 15(17), pp. 1689-1695, (Dec. 2004).
Shimoda, T. et al., "Solution-Processed Silicon Films and Transistors," Nature, vol. 440(7085), pp. 783-786, (Apr. 2006).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010).
Han, "Energy Band Gap Engineering of Graphene Nanoribbons," Physical Review Letters, vol. 98, pp. 1-7, (May 16, 2007).
Prins et al., "Room-Temperature Gating of Molecular Junctions Using Few-Layer Graphene Nanogap Electrodes," Nano Letters, vol. 11, pp. 4607-4611, (Oct. 21, 2011).
Heerema et al., "Graphene Nanodevices for DNA Sequencing," Nature Nanotechnology, vol. 11, pp. 127-136, (Feb. 3, 2016).
Liu et al., "Atomically Thin Molybdenum Disulfide Nanopores with High Sensitivity for DNA Translocation," ACS Nano, vol. 8, pp. 2504-2511, (Feb. 18, 2014).
Kim et al., "Rapid Fabrication of Uniformly Sized Nanopores and Nanopore Arrays for Parallel DNA Analysis," Advances Materials, vol. 18, pp. 3149-3153, (Dec. 4, 2006) (Abstract Only).
Wang et al., "Electronics and Optoelectronics of Two-Dimensional Transition Metal Dichalcogenides," Nature Nanotechnology, vol. 7, pp. 699-712, (Nov. 6, 2012).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Science, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
USPTO; Final Office Action dated Jul. 10, 2018 in U.S. Appl. No. 15/050,270.
USPTO; Final Office Action dated Jul. 10, 2018 in U.S. Appl. No. 15/728,400.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
Hanief, Topic, Pineda-Vargas, "Solid State Dewetting of Continuous Thin Platinum Coatings," Nuclear Instruments and Methods in Physics Research, vol. 363, pp. 173-176, (2015).
Sholders et al., "Distinct Conformations of a Putative Translocation Element in Poliovirus Polymerase," Journal of Molecular Biology, vol. 426(7), pp. 1407-1419, (Apr. 3, 2014).
USPTO; Advisory Action dated Sep. 4, 2018 in U.S. Appl. No. 15/796,080.
USPTO; Notice of Allowance dated Sep. 12, 2018 in U.S. Appl. No. 15/728,412.
USPTO; Advisory Action dated Sep. 26, 2018 in U.S. Appl. No. 15/050,270.
USPTO; Notice of Allowance dated Oct. 11, 2018 in U.S. Appl. No. 15/796,080.
USPTO; Advisory Action dated Oct. 12, 2018 in U.S. Appl. No. 15/728,400.
USPTO; Requirement for Restriction dated Oct. 15, 2018 in U.S. Appl. No. 16/015,028.
PCT; International Preliminary Report on Patentability dated Aug. 14, 2018 in Application No. PCT/US2017/017231.

(56) References Cited

OTHER PUBLICATIONS

USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Advisory Action dated Nov. 14, 2018 in U.S. Appl. No. 15/728,400.
USPTO; Notice of Allowance dated Dec. 6, 2018 in U.S. Appl. No. 15/728,400.
USPTO; Requirement for Restriction dated Dec. 17, 2018 in U.S. Appl. No. 16/015,049.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.
PCT; International Search Report dated Nov. 9, 2018 in Application No. PCT/US2018/048873.
PCT; Written Opinion dated Nov. 9, 2018 in Application No. PCT/US2018/048873.
Braun et al., "DNA-Templated Assembly and Electrode Attachment of a Conducting Silver Wire," Letters to Nature, vol. 391(6669), pp. 775-778, (Feb. 1998).
Chen et al., "Electrochemical Approach for Fabricating Nanogap Electrodes with Well Controllable Separation," Applied Physics Letters, vol. 86, pp. 123105.1-123105.3, (2005).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Iqbal et al., "Direct Current Electrical Characterization of ds-DNA in Nanogap Junctions," Applied Physics Letter, vol. 86, p. 153901-1-153901-3, (Apr. 2005).
Liu et al., "Controllable Nanogap Fabrication on Microchip by Chronopotentiometry," Electrochimica Acta, vol. 50, pp. 3041-3047, (2005).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reichert et al., "Driving Current Through Single Organic Molecules," Physical Review Letters, vol. 88(17), pp. 176804-1-176804-4, (Apr. 2002).
Reed et al., "Conductance of a Molecular Junction Reports," Science, vol. 278, pp. 252-254, (Oct. 1997).
Roppert et al., "A New Approach for an Interdigitated Electrodes DNA-Sensor," Bioelectrochemistry, (2005).
Kraft, "Doped Diamond: A Compact Review on a New, Versatile Electrode Material," International Journal of Electrochemistry, (May 2007), 2, 355-385.
USPTO; Non-Final Office Action dated Mar. 6, 2019 in U.S. Appl. No. 16/015,049.
USPTO; Non-Final Office Action dated Mar. 7, 2019 in U.S. Appl. No. 15/944,356.
USPTO; Final Office Action dated Apr. 15, 2019 in U.S. Appl. No. 16/015,028.
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).
Khawli et al., "Charge Variants in IgG1-Isolation, Characterization, In Vitro Binding Properties and Pharmacokinetics in Rats," Landes Bioscience, vol. 2(6), pp. 613-623, (2010).
Schaefer et al., "Stability and Dewetting Kinetics of Thin Gold Films on Ti, TiOx, and ZnO Adhesion Layers," Acta Materiaha, vol. 61, pp. 7841-7848, (2013).
USPTO; Advisory Action dated May 22, 2019 in U.S. Appl. No. 15/979,135.
USPTO; Restriction Requirement dated May 29, 2019 in U.S. Appl. No. 16/250,929.
USPTO; Notice of Allowance dated May 30, 2019, U.S. Appl. No. 16/152,190.
PCT; International Search Report and Written Opinion dated Jan. 18, 2019 in Application No. PCT/US2018/055264.
EP; European Search Report dated Jan. 30, 2019 in Application No. EP16815467.2.
CN; Notice of the First Office Action dated Sep. 2, 2019 in Chinese Application No. 201680049272.8.
USPTO; Final Office Action dated Jun. 19, 2019 in U.S. Appl. No. 16/015,049.
USPTO; Final Office Action dated Jul. 10, 2019 in U.S. Appl. No. 15/050,270.
USPTO; Non-Final Office Action dated Jul. 30, 2019 in the U.S. Appl. No. 16/015,028.
USPTO; Non-Final Office Action dated Aug. 22, 2019 in the U.S. Appl. No. 16/011,065.
USPTO; Restriction Requirement dated Sep. 19, 2019 in U.S. Appl. No. 16/073,706.
USPTO; Non-Final Office Action dated Aug. 19, 2019 in U.S. Appl. No. 12/667,583.
EP; European Search Report dated Aug. 2, 2019 in Application No. EP16885434.7.
EP; European Search Report dated Aug. 2, 2019 in Application No. EP17745026.9.
Thompson "Solid-State Dewetting of Thin Films" Annual Review of Materials Research, vol. 42, pp. 399-434 (2012).
USPTO; Notice of Allowance dated Oct. 23, 2019 in U.S. Appl. No. 16/250,929.
USPTO; Non-Final Office Action dated Oct. 24, 2019 in U.S. Appl. No. 16/073,706.
USPTO; Notice of Allowance dated Nov. 8, 2019 in U.S. Appl. No. 16/015,028.
USPTO; Non-Final Office Action dated Nov. 5, 2019 in U.S. Appl. No. 16/015,049.
USPTO; Notice of Allowance dated Jan. 6, 2020 in U.S. Appl. No. 15/050,270.
USPTO; Non-Final Office Action dated Jan. 10, 2020 in U.S. Appl. No. No. 16/076,673.
EP; European Search Report dated Oct. 24, 2019 in Application No. 17757146.

* cited by examiner

MULTI-ELECTRODE MOLECULAR SENSING DEVICES AND METHODS OF MAKING THE SAME

CROSS-REFERENCE TO RELATED APPLICATIONS

This application is a divisional of U.S. Non-Provisional patent application Ser. No. 15/796,080, filed on Oct. 27, 2017, which issued as U.S. Pat. No. 10,151,722 on Dec. 11, 2018, and which is a continuation of application Ser. No. 15/220,307, filed Jul. 26, 2016, which issued as U.S. Pat. No. 9,829,456 on Nov. 28, 2017, the disclosures of which are incorporated herein by reference in their entirety.

FIELD

The present disclosure relates to nanofabrication and nanoelectronics. More particularly, the present disclosure relates to devices, and the fabrication of devices for sensing and analyzing molecules, including genome sequencing and DNA sequencing.

BACKGROUND

Molecular analysis has received an increasing amount of attention in various fields such as precision medicine or nanotechnology. One example includes the analysis of molecules for sequencing genomes. The seminal work of Avery in 1946 demonstrated that DNA was the material that determined traits of an organism. The molecular structure of DNA was then first described by Watson and Crick in 1953, for which they received the 1962 Nobel Prize in Medicine. This work made it clear that the sequence of chemical letters (bases) of the DNA molecules encode the fundamental biological information. Since this discovery, there has been a concerted effort to develop means to actually experimentally measure this sequence. The first method for systematically sequencing DNA was introduced by Sanger in 1978, for which he received the 1980 Nobel Prize in Chemistry.

A basic method for sequencing a genome was automated in a commercial instrument platform in the late 1980's, which ultimately enabled the sequencing of the first human genome in 2001. This was the result of a massive public and private effort taking over a decade, at a cost of billions of dollars, and relying on the output of thousands of dedicated DNA sequencing instruments. The success of this effort motivated the development of a number of "massively parallel" sequencing platforms with the goal of dramatically reducing the cost and time required to sequence a human genome. Such massively parallel sequencing platforms generally rely on processing millions to billions of sequencing reactions at the same time in highly miniaturized microfluidic formats. The first of these was invented and commercialized by Rothberg in 2005 as the 454 platform, which achieved thousand fold reductions in cost and instrument time. However, the 454 platform still required approximately a million dollars and took over a month to sequence a genome.

The '454 platform was followed by a variety of other related techniques and commercial platforms. This progress lead to the realization of the long-sought "$1,000 genome" in 2014, in which the cost of sequencing a human genome at a service lab was reduced to approximately $1,000, and could be performed in several days. However, the highly sophisticated instrument for this sequencing cost nearly one million dollars, and the data was in the form of billions of short reads of approximately 100 bases in length. The billions of short reads often further contained errors so the data required interpretation relative to a standard reference genome with each base being sequenced multiple times to assess a new individual genome.

Thus, further improvements in quality and accuracy of sequencing, as well as reductions in cost and time are still needed. This is especially true to make genome sequencing practical for widespread use in precision medicine, where it is desirable to sequence the genomes of millions of individuals with a clinical grade of quality.

While many DNA sequencing techniques utilize optical means with fluorescence reporters, such methods can be cumbersome, slow in detection speed, and difficult to mass produce to further reduce costs. Label-free DNA or genome sequencing approaches provide advantages of not having to use fluorescent type labeling processes and associated optical systems, especially when combined with electronic signal detection that can be achieved rapidly and in an inexpensive way.

In this regard, certain types of molecular electronic devices can detect single molecule, biomolecular analytes such as DNAs, RNAs, proteins, and nucleotides by measuring electronic signal changes when the analyte molecule is attached to a circuit. Such methods are label-free and thus avoid using complicated, bulky and expensive fluorescent type labeling apparatus.

While current molecular electronic devices can electronically measure molecules for various applications, they lack the scalability and manufacturability needed for rapidly sensing many analytes at a scale of up to millions in a practical manner. Such highly scalable methods are particularly important for DNA sequencing applications, which often need to analyze millions to billions of independent DNA molecules. In addition, the manufacture of current molecular electronic devices is generally costly due to the high level of precision needed.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

DETAILED DESCRIPTION

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

Figure 1A:
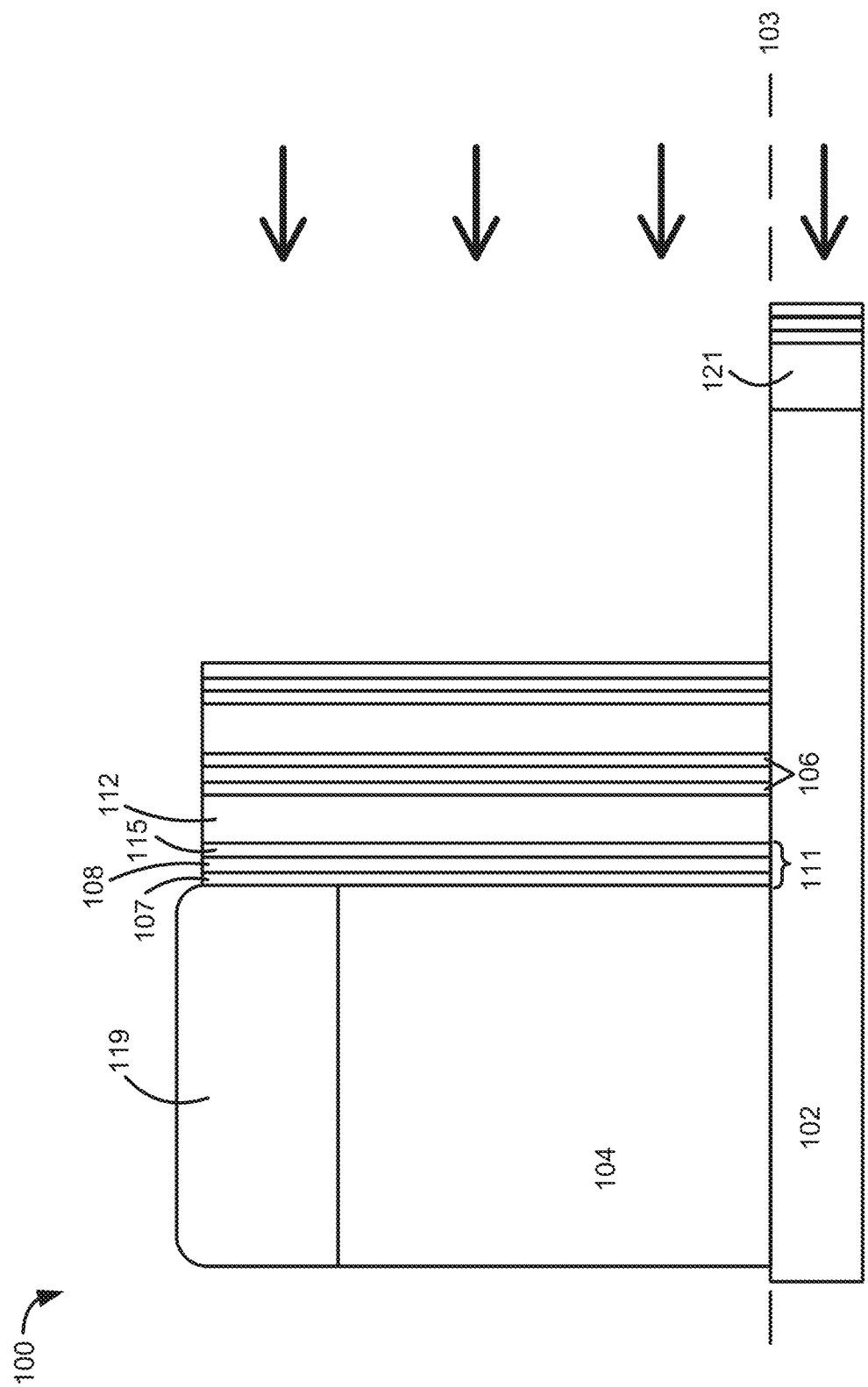
FIG. 1A is a cross section view showing fabrication of a molecular sensor by sequentially depositing tri-layer thin film device stacks using a low deposition angle and a sacrificial top layer according to an embodiment.
Figure 1B:
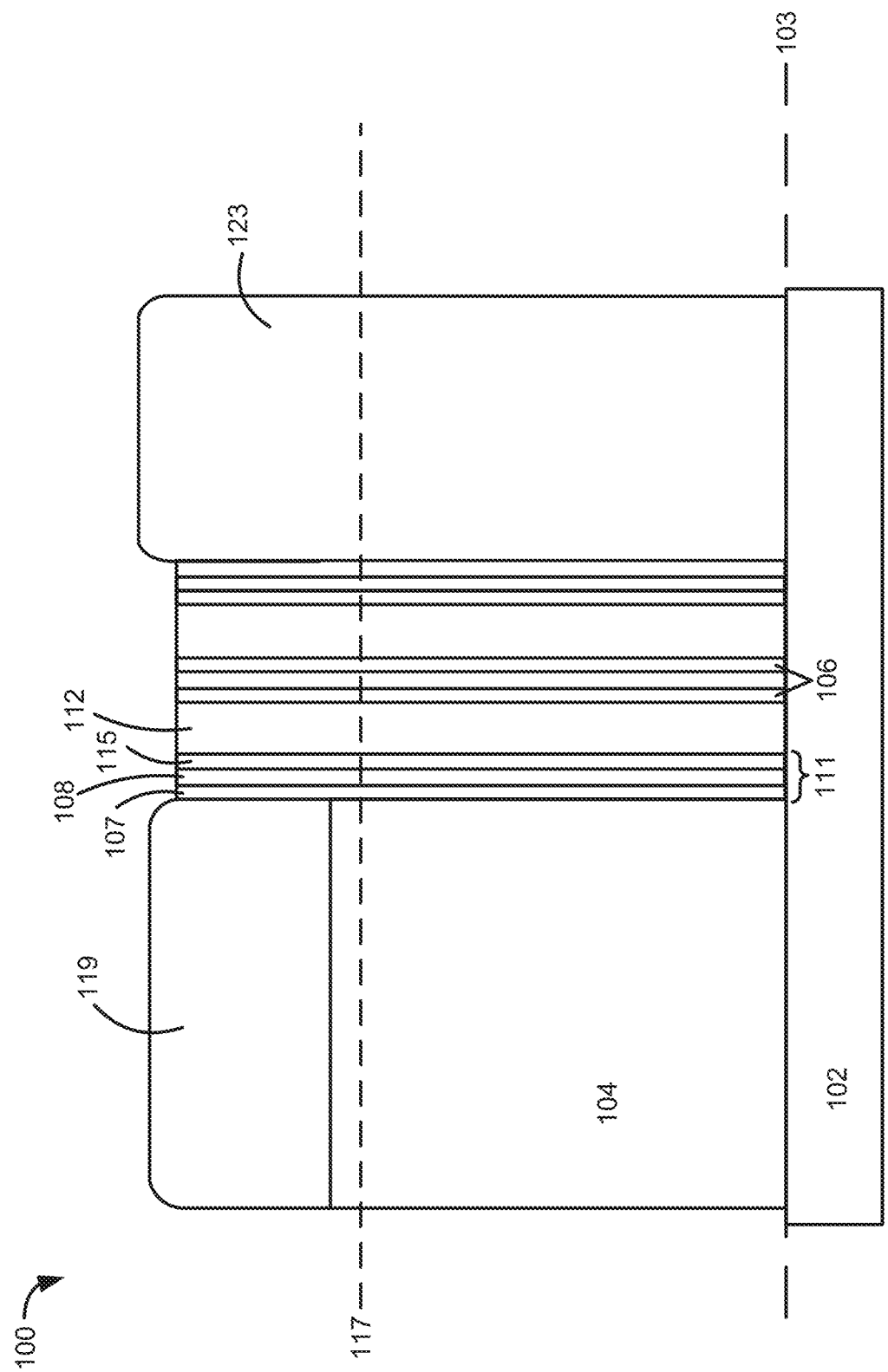
FIG. 1B is a cross section view showing further fabrication of the molecular sensor of FIG. 1A.
Figure 1C:
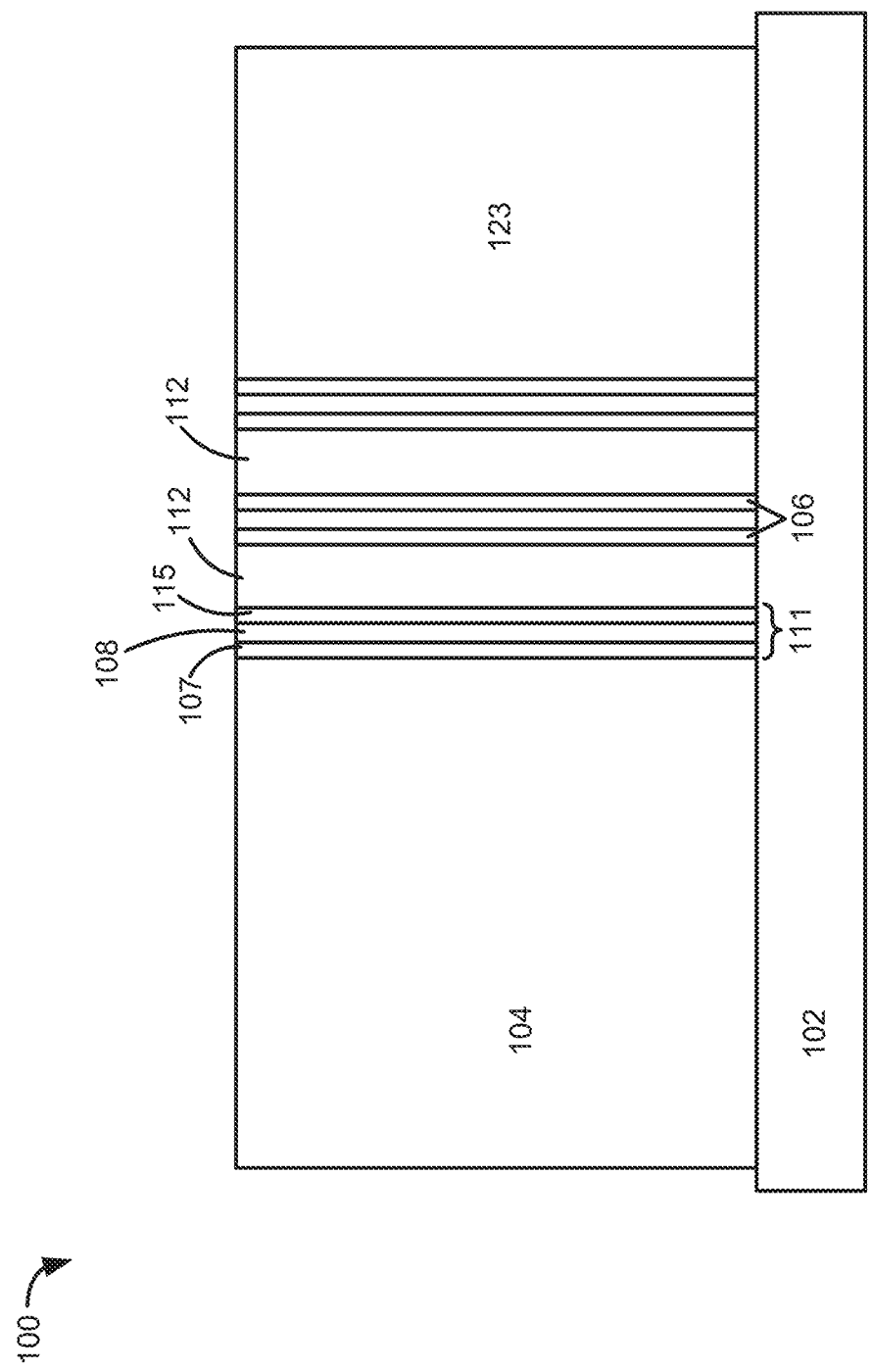
FIG. 1C is a cross section view of the molecular sensor of FIGS. 1A and 1B after fabrication.

The cross-section views of FIGS. 1A to 1C illustrate an example fabrication process of a molecular sensor 100 by using a low deposition angle or by a sideways incident film deposition of thin films and thick films, relative to a substrate plane 103. A tri-layer thin film structure or device stack 111 is sequentially deposited with a first electrode sheet 107, an inner dielectric sheet 108, and a second electrode sheet 115. The tri-layer deposition is repeated with a thicker, separating outer dielectric sheet 112 deposited between adjacent tri-lalyer device stacks 111 according to an embodiment.

As shown in FIGS. 1A to 1C, sensor 100 includes a supporting substrate 102 with a protrusion 104 protruding from the substrate 102 at an angle to a substrate plane 103 defined by the substrate 102. The supporting substrate 102 can include, for example, $SiO_2$ or Si with a $SiO_2$ coating. In the example of FIG. 1, the protrusion 104 is a block that extends from the substrate 102 perpendicular to the substrate plane 103. In other implementations, the protrusion 104 may protrude from the substrate 102 at a different angle such as a 45 or 60 degree angle.

The protrusion 104 includes a dielectric such as $SiO_2$, $Al_2O_3$, or MgO, for example. In some implementations, the protrusion 104 can be formed by removing portions of the substrate 102 or by attaching the dielectric block of protrusion 104 to the substrate 102. The protrusion 104 can provide structural support for depositing dielectric and electrode layers at an angle to the substrate plane 103.

FIG. 1A represents a thin film and thick film deposition process using sacrificial top and side layers 119 to enable sideways deposition of multiple tri-layer device stacks 111. In the example of FIG. 1A, the deposition angle can be horizontal as shown by the arrows on the right side of FIG. 1A, or may be within plus or minus 20 degrees from horizontal. A first conductive electrode sheet 105 is thin film deposited at a sideways or low deposition angle, followed by an inner dielectric sheet 108, and then a second electrode sheet 115. This process can be repeated to form many device stacks 111, each including a pairs of electrode sheets 106 with an inner dielectric sheet 108 between the pair of electrode sheets 106.

A thicker dielectric sheet 112 is deposited between each tri-layer device stack. The relative size shown for the tri-layer device stacks 111 may be somewhat exaggerated to better illustrate the features of the tri-layer device stacks 111. In this regard, the cross section width of the tri-layer device stacks in some embodiments may be less than 50 nm.

FIG. 1B illustrates the addition of a mechanically supportive block material 123 to facilitate polishing of the material from the top and planarizing the device array structure along plane 117. Block material 123 can include, for example, an oxide or a precursor of oxide (e.g., hydrogen silsesquioxane (HSQ)). FIG. 1C provides a cross section view of the molecular sensor 100 after planarizing along plane 117.

Figure 2A:
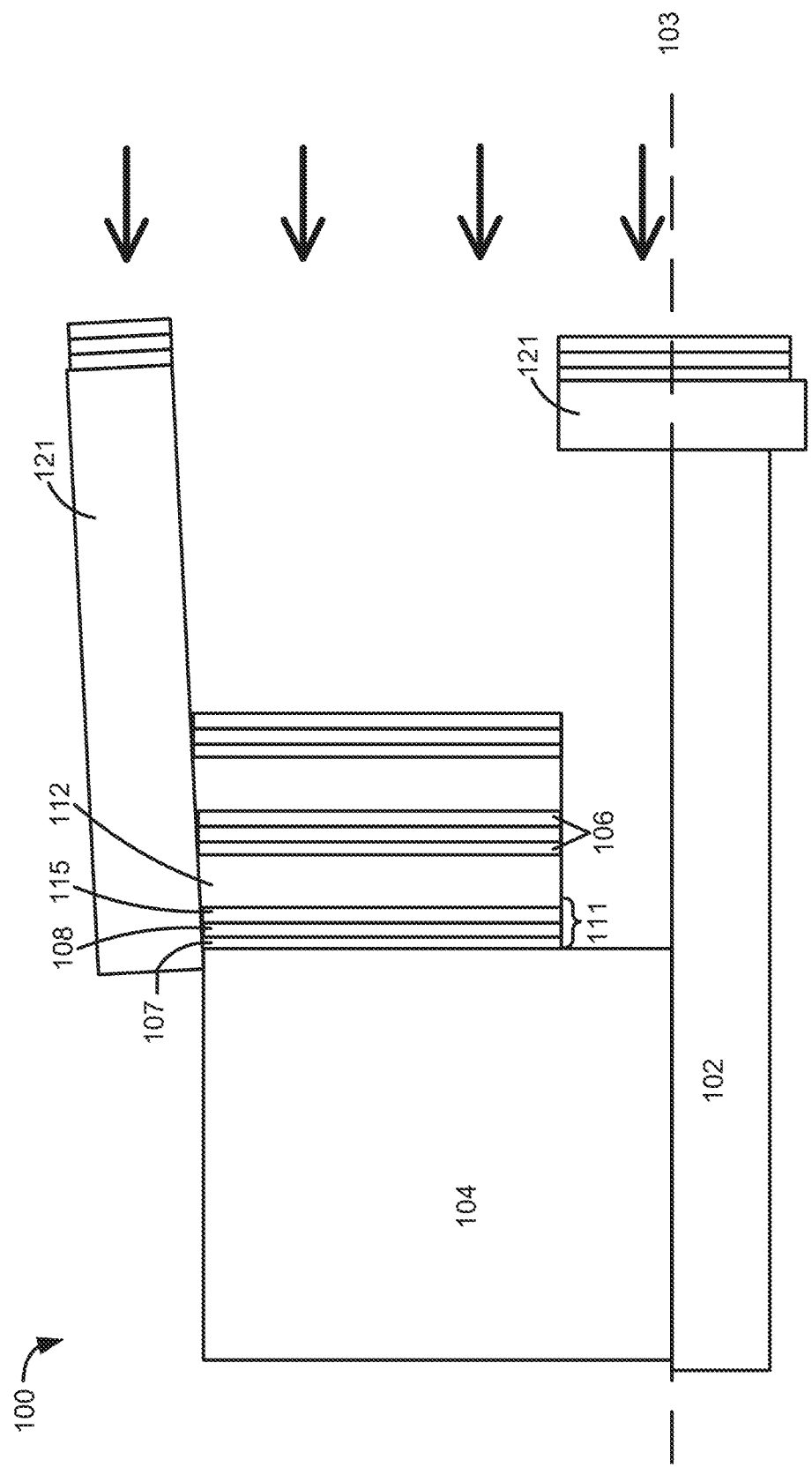
FIG. 2A is a cross section view showing fabrication of a molecular sensor by sequentially depositing tri-layer thin film device stacks using a low deposition angle and detachable shades according to an embodiment.

FIG. 2A demonstrates use of detachable top and side shades 121 to enable sideways or low angle deposition of multiple tri-layer thin film device stacks 111. A first conductive electrode sheet 105 is thin film deposited at a low deposition angle, followed by an inner dielectric thin film sheet 108, and then a second electrode sheet 115. This process is repeated to form multiple device stacks 111, with a thicker dielectric separator sheet 112 deposited between adjacent tri-layer stacks 111.

Figure 2B:
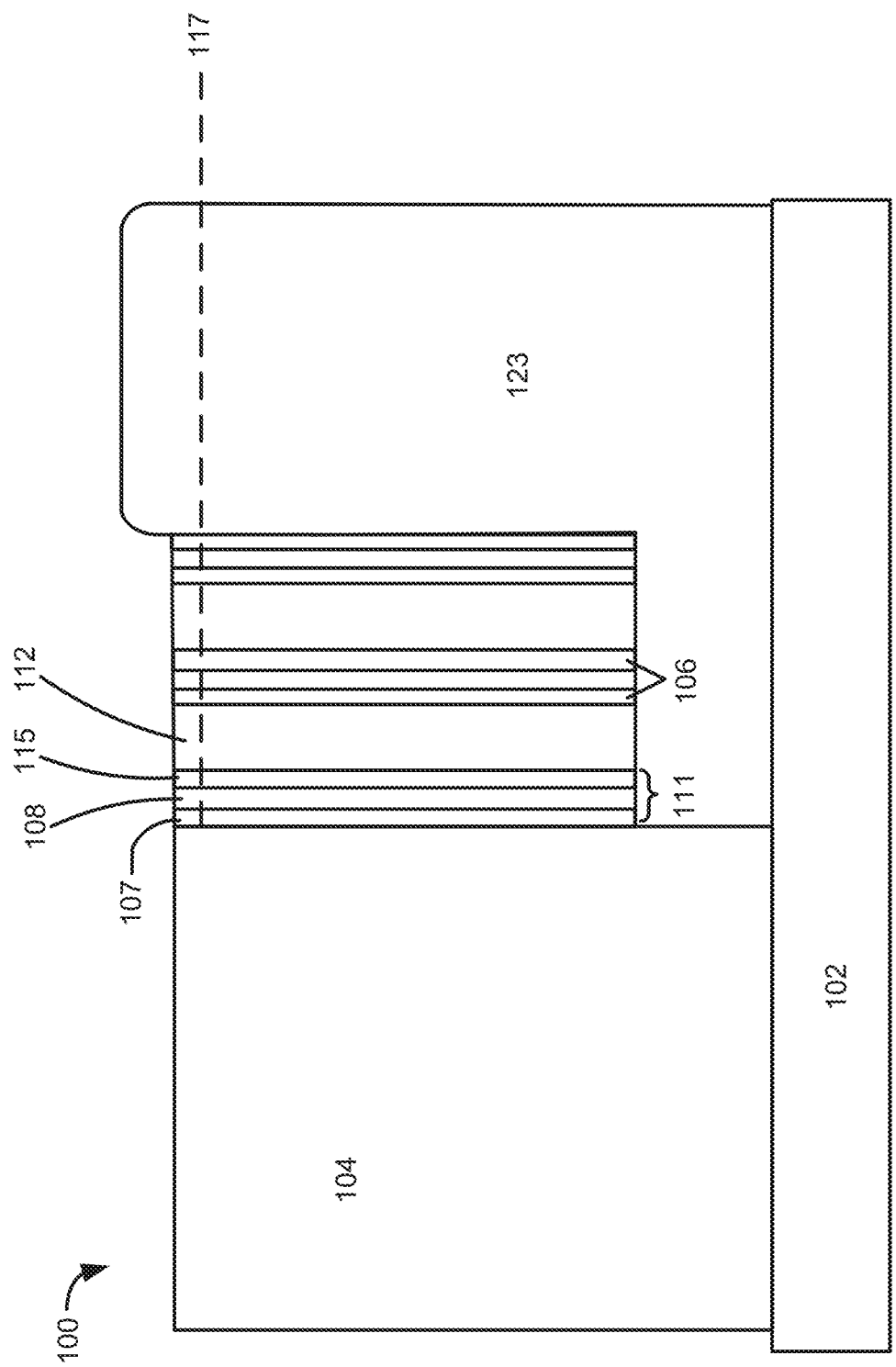
FIG. 2B is a cross section view showing further fabrication of the molecular sensor of FIG. 2A.
Figure 2C:
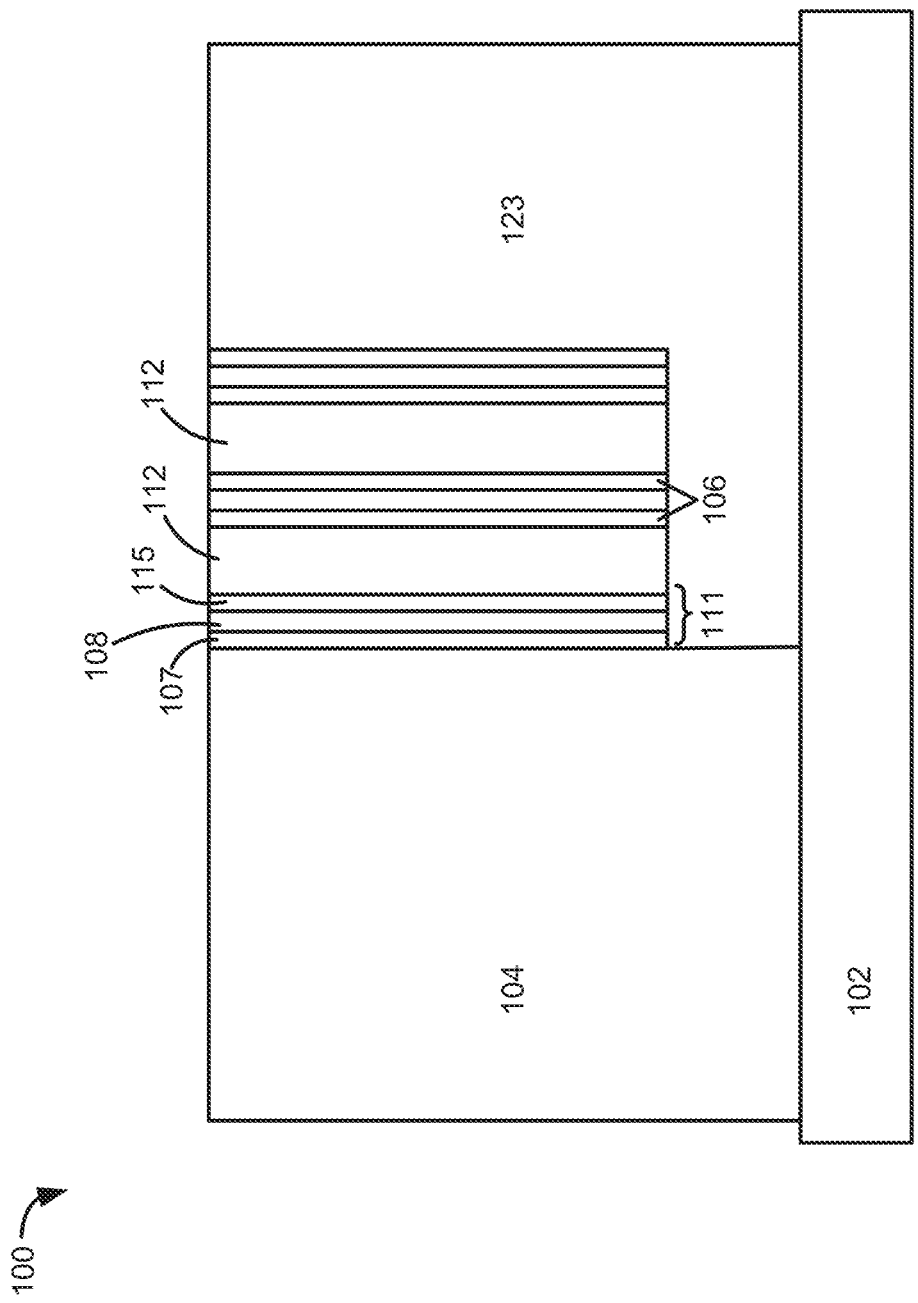
FIG. 2C is a cross section view of the molecular sensor of FIGS. 2A and 2B after fabrication.

FIG. 2B illustrates the addition of a mechanically supportive block material 123 such as oxide or precursor of oxide (e.g., HSQ) to the structure of FIG. 2A after removal of the shades 121. The supportive block material 123 can facilitate polishing of the material from the top and planarizing the device array structure along plane 117. FIG. 2C provides a cross section view of the molecular sensor 100 after planarizing along plane 117.

The molecular sensors 100 as shown in the examples of FIGS. 1C and 2C utilize a unique geometry of electrodes in a vertically aligned tri-layer sheet configuration. The sheet geometry of the electrically conductive electrodes ordinarily allows for a low electrical resistance of the sensor electrodes to enable a desirably high signal-to-noise ratio, with accurate dimensional control, and ease of scale-up fabrication at a relatively low cost. This configuration can facilitate the packing of high-density device arrays using a low device surface area real estate, allowing the manufacture of a multiple device assembly. The deposition of conductor layer, dielectric layer, and second conductor layer can be repeated many times. In this regard, this sequence of deposition may be repeated 2 to 10,000 times to produce an array of 2 to 10,000 parallel devices.

The tri-layer device stack 111 can include highly electrically conductive metallic electrode sheets in a vertical or near-vertical configuration. Other implementations can include a tilted angle orientation of up to about a 60 degree tilting of the electrode sheets from a vertical alignment, but preferably with less than 20 degrees of tilting. Each pair of electrode sheets 106 is separated in the device stack 111 by a dielectric sheet layer material 108 that can be selected from oxides (e.g., $SiO_2$, $Al_2O_3$, MgO, CaO, refractory oxide, rare earth oxide or a mixture of oxides), nitrides (e.g., AlN, $Si_3N_4$, refractory nitride, rare earth nitride or a mixture of nitrides), fluoride, oxyfluoride, or oxynitride.

The material for the electrodes 107 and 115 is desirably selected from high-conductivity metals or alloys such as Au, Pt, Pd, Ag, Os, Ir, Rh, Ru and their alloys. The dimension of the exposed electrode sheet on the device top surface can have a thickness or width, for example, of 2 to 100 nm. Depending on design considerations such as the molecule to be analyzed, the electrode sheets 107 and 115 in FIGS. 1A and 2A can be deposited with a thickness of 1 to 40 nm or preferably 5 to 15 nm, with the height of a vertical or near-vertical electrode sheet being desirably at least 100 μm tall, preferably at least 1,000 μm tall, and even more preferably at least 10,000 μm tall. Accordingly, the desired aspect ratio of the electrode sheet, in terms of height to thickness, is at least 10,000, and preferably at least 100,000.

In some implementations, a thin adhesion enhancing layer may be deposited at the interface between the electrode sheets and the inner dielectric sheet to improve the adhesion at the interface. In one example, a 1 to 5 nm thick film material is deposited at the interface using a material such as Ti, Cr, Al, Zr. Mo, Nb, Ta, or Hf.

The dimension of the exposed dielectric sheet 108 between the two electrode sheets on the device top surface is desirably in the range of 1 to 40 nm thick or wide, and preferably 5 to 15 nm thick. In some implementations, the thickness of the inner dielectric sheets 108 can be at most 10 nm. The height of a vertical or near-vertical dielectric sheet 108 is desirably at least 100 μm tall, preferably at least 1,000 μm tall, and even more preferably at least 10,000 μm tall. Accordingly, the desired aspect ratio of the inner dielectric layer sheet, in terms of height to thickness, is at least 10,000, and preferably at least 100,000.

The dimension of the outer dielectric layer 112 that separates neighboring tri-layer device stacks 111, has a desirable thickness (or width) range of at least 500 to 20,000 nm that is at least one order of magnitude greater than the thickness of the inner dielectric sheet. A preferred thickness for the outer dielectric layer 112 can be, for example, in the range of 500 to 5,000 nm. The separation between adjacent tri-layer device stacks 111 reduces electrical, inductive, capacitive, or other interferences.

As discussed in more detail below with reference to FIG. 3, the molecular sensor 100 can be formed using a low incident angle oblique deposition of layers, such as at a deposition angle of 0 to less than plus or minus 20 degrees from the substrate plane 103. In the example process of FIG. 3, a low incident angle oblique deposition is used with one or more sacrificial layers (e.g., sacrificial layers 119 in FIG. 1A) and/or detachable shades (e.g., detachable shades 121 in FIG. 2A) to help prevent deposition of the electrode and dielectric layers on certain surfaces. The sacrificial layers and detachable shades are later removed after the electrode and dielectric sheets have been formed at an angle to the substrate plane 103.

In the example of FIG. 1A, a series of film depositions are performed at a deposition angle of 0 to less than plus or minus 20 degrees from the substrate plane 103. The sacrificial layer 119 acts as a dummy, disposable material on a surface of the protrusion 104 opposite the substrate 102. In some implementations, the sacrificial layer 119 can include a slight extension off the edge of the protrusion 104 to help prevent deposition above the top surface of the protrusion 104.

Figure 4A:
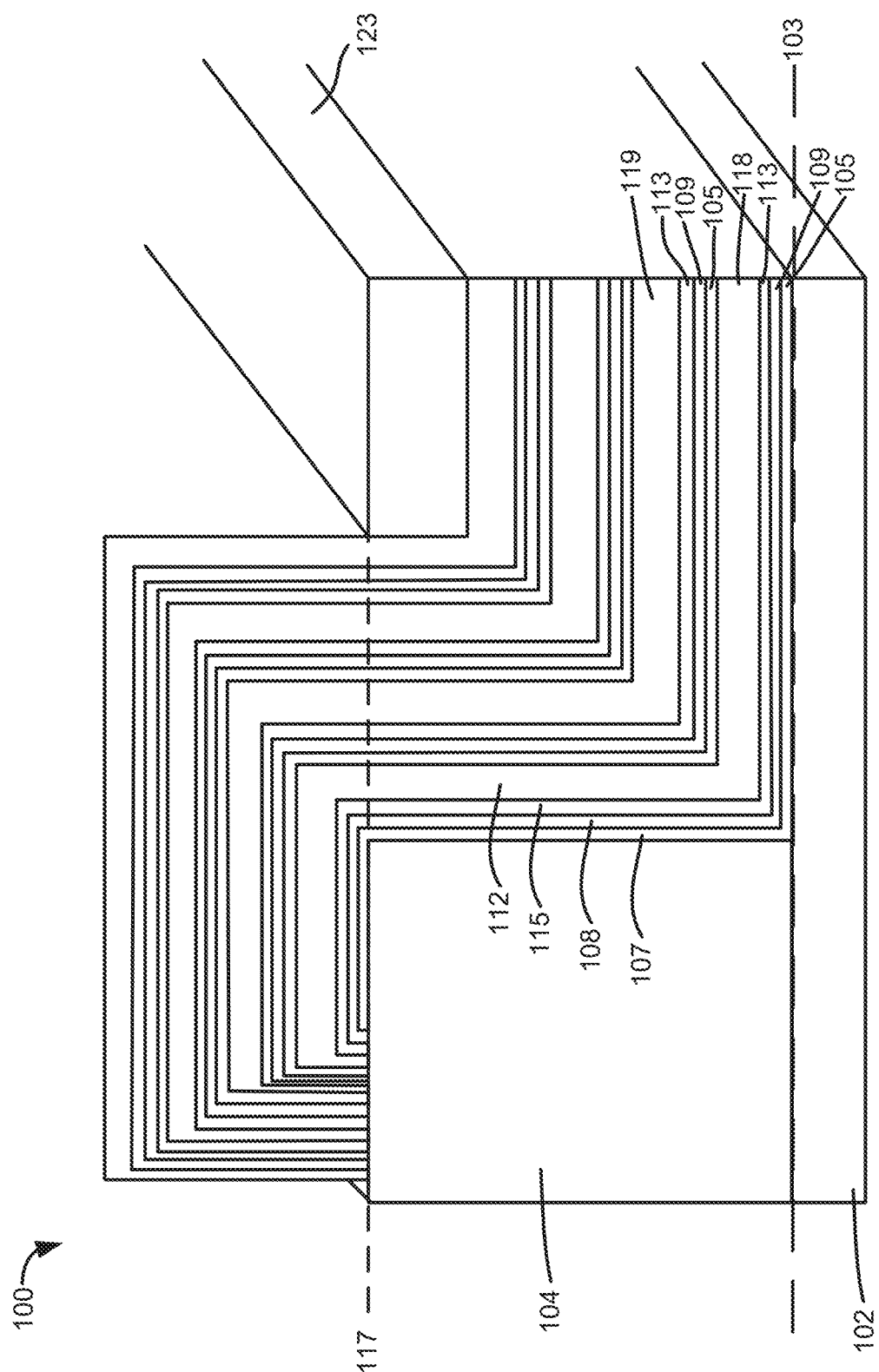
FIG. 4A is a cross section view showing fabrication of a molecular sensor by sequentially depositing tri-layer thin film device stacks using a high deposition angle according to an embodiment.
Figure 4B:
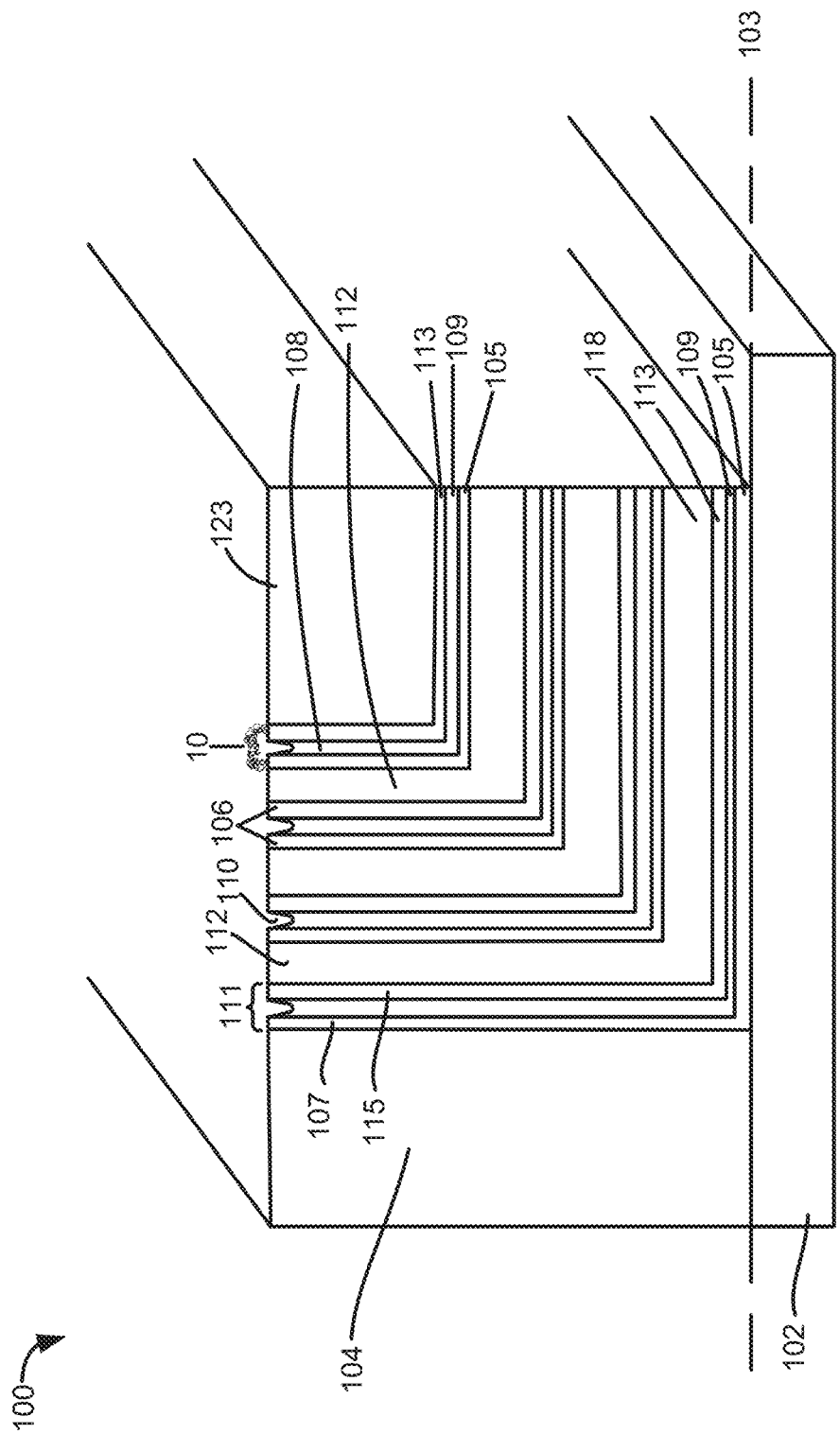
FIG. 4B is a cross section view of the molecular sensor of FIG. 4A after fabrication.
Figure 5:
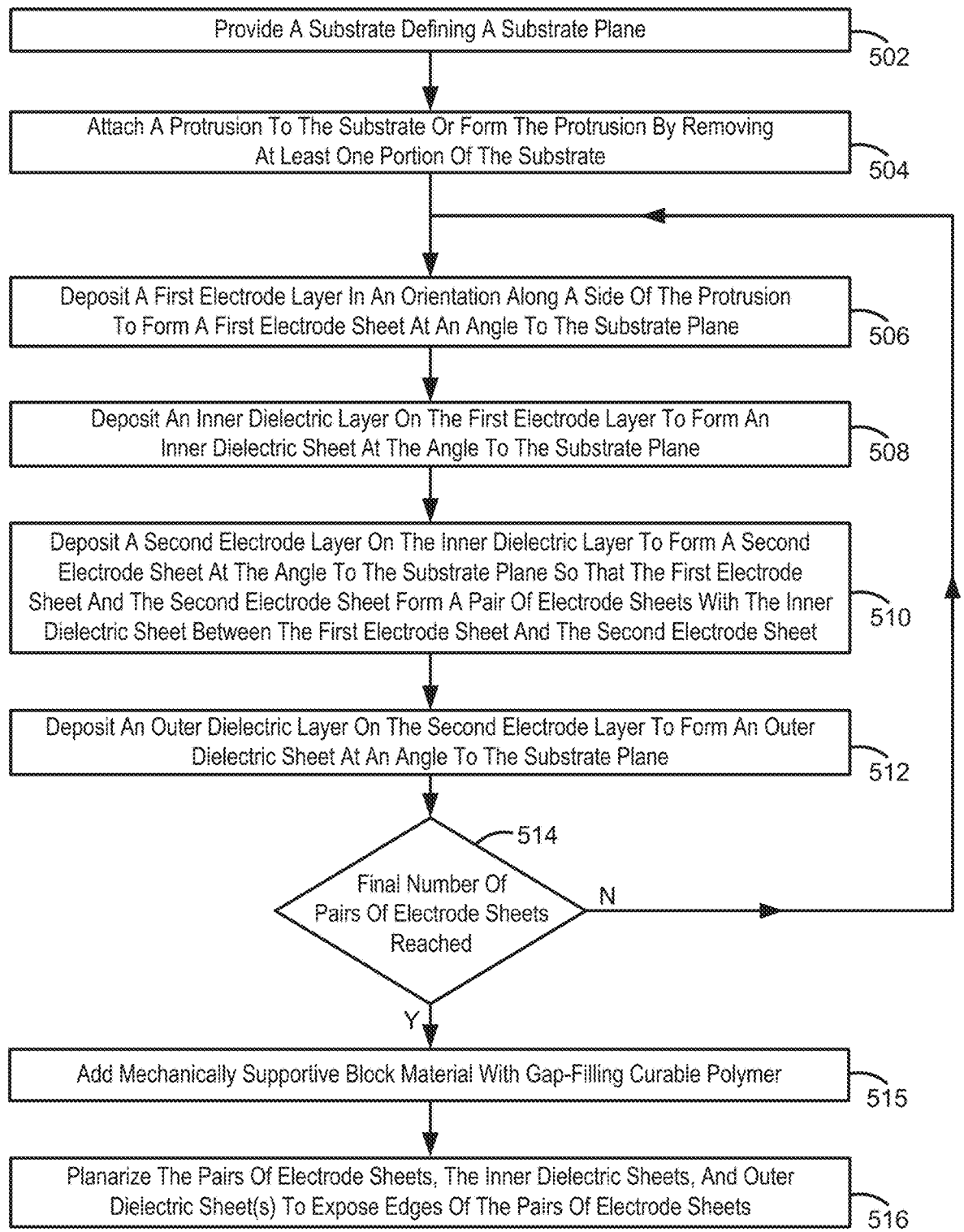
FIG. 5 is a flowchart for a manufacturing process of the molecular sensor of FIG. 4B according to an embodiment utilizing high incident angle oblique deposition.

FIG. 5 discussed below provides an alternative example process that includes performing the multilayer deposition at a higher oblique incident angle and followed by planarization. The higher oblique incident angle for multilayer deposition can be performed, for example, at any angle in the range of 20 to 70 degrees from the substrate plane 103, with a preferred deposition angle between 30 degrees and 60 degrees. With an oblique angle deposition without a sacrificial layer as in the process of FIG. 5, the surface of the protrusion 104 opposite the substrate 102 is also covered with multilayer thin films, as illustrated in FIG. 4A. A planarization polishing process, after the attachment of a mechanically supportive block material, removes the film deposition on the surface of the protrusion 104 opposite the substrate 102 so as to achieve a structure as in FIG. 4B.

Figure 3:
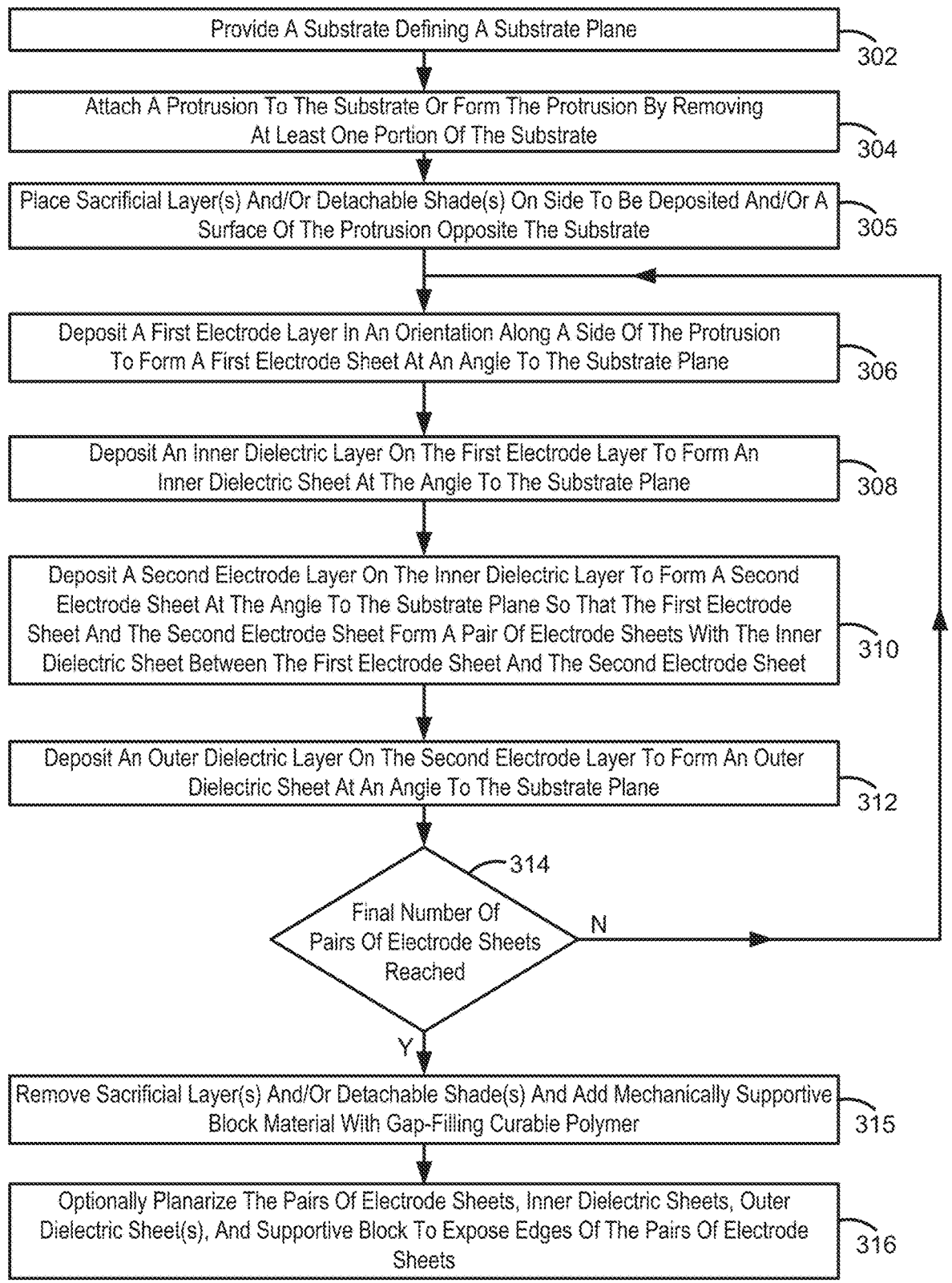
FIG. 3 is a flowchart for a manufacturing process of the molecular sensor of FIG. 1C or FIG. 2C according to an embodiment utilizing low incident angle oblique deposition.

With reference to the flowchart of FIG. 3, in block 302, a substrate such as the substrate 102 is provided defining a substrate plane. The substrate plane can be defined by being parallel with a surface of the substrate such as a top or bottom surface for supporting dielectric and electrode layers.

In block 304, a protrusion (e.g., protrusion 104) is attached to the substrate or the protrusion is formed by removing one or more portions of the substrate. As noted above, the protrusion extends or protrudes from the substrate plane at an angle, such as 90 degrees. In one example, the protrusion can be a cut-out step of an initially thicker supporting substrate. In another example, a dielectric block or other shape may be attached to a supporting substrate to form the protrusion at an angle to the substrate plane.

With reference to FIG. 3, in block 305, one or more sacrificial layers and/or detachable shades are placed on a side to be deposited (e.g., detachable shades 121 in FIG. 2A) and/or a surface of the protrusion opposite the substrate (e.g., the top sacrificial layer 119 in FIG. 1A). As noted above, the sacrificial layer may extend beyond the edge of the protrusion 104. The sacrificial layer can include, for example, a physically removable plate, or a dissolvable polymer layer, such as acetone-dissolvable polymethyl methacrylate (PMMA) that is often used for lift-off processing in semiconductor fabrication. The detachable shade can include, for example, a detachable metallic, ceramic, or polymer material.

In block 306, a first electrode layer is deposited on the substrate. At least a portion of the first electrode layer is deposited in an orientation along a side of the protrusion to form a first electrode sheet (e.g., first electrode sheet 107 in FIG. 1A or in FIG. 2A) at the angle to the substrate plane. In other implementations, an initial dielectric layer may be deposited before the first electrode layer is deposited in block 306.

In the example process of FIG. 3, an inner dielectric layer is deposited in block 308 on the first electrode layer deposited in block 306. As shown in the examples of FIGS. 1A and 2A, at least a portion of the inner dielectric layer is deposited in the orientation along the protrusion 104 to form the inner dielectric sheet 108 at the angle to the substrate plane 103. As with the first electrode layer deposited in block 306, oblique incident deposition can be used to deposit the inner dielectric layer at the angle to the substrate plane. Standard complementary metal-oxide semiconductor (CMOS) processes such as oblique incident deposition can ordinarily allow for the inner dielectric layer to be deposited with an accurate and repeatable thickness.

In some implementations, a thin adhesion enhancing layer may be deposited on the first electrode layer before and/or after depositing the inner dielectric layer to improve adhesion of the layers. In one example, a 1 to 5 nm thick film material is deposited at the interface using a material such as Ti, Cr, Al, Zr. Mo, Nb, Ta, or Hf.

In block 310, a second electrode layer is deposited on the inner dielectric layer to form a second electrode sheet (e.g., second electrode sheet 115 in FIGS. 1A and 2A) at the angle to the substrate plane, using, for example, oblique incident deposition. The first electrode sheet and the second electrode sheet form a pair of electrode sheets with the inner dielectric sheet between the first electrode sheet and the second electrode sheet.

In block 312, an outer dielectric layer is deposited on the second electrode layer to form an outer dielectric sheet at an angle to the substrate plane. With reference to the examples in FIGS. 1A and 2A, the outer dielectric layer is deposited on the second electrode layer to form the outer dielectric sheet 112 at an angle to the substrate plane 103. In some implementations, the outer dielectric layer may have a different thickness if it is a final outer dielectric layer to, for example, facilitate packaging of the sensor in a larger array of sensors or to provide a greater exterior insulation.

In block 314, it is determined whether a final number of pairs of electrode sheets has been reached. In some implementations, the final number of pairs of electrode sheets may be as few as two pairs of electrode sheets. In this regard, the sub-process of blocks 306 to 312 is repeated at least once to provide for at least two pairs of electrode sheets. In some implementations, the final number of pairs of electrode sheets may be as large as several thousand pairs of electrode sheets for example. The final number of pairs of electrode sheets may depend on the design considerations for the sensor being manufactured, such as a desired testing speed, a type of molecule to be analyzed, or a desired footprint for the sensor.

If the final number of pairs of electrode sheets has not been reached in block 314, the process returns to block 306 to deposit another first electrode layer in an orientation along a side of the protrusion to form another first electrode sheet at an angle to the substrate plane.

On the other hand, if the final number of pairs of electrode sheets has been reached in block 314, the process proceeds to block 315 to remove sacrificial layers or detachable shades added in block 305 above. The sacrificial layer can, for example, be physically removed or removed by dissolving the sacrificial layer and the detachable shade can be physically removed. In one example, the sacrificial layer is dissolved using a liquid, as in lift-off processing.

At least one mechanically supportive block material is also added in block 315 with a gap-filling curable polymer. A mechanically supportive block material may be attached adjacent the deposited multilayer stack (e.g., block 123 added to the right of the deposited layers shown in FIGS. 1B and 2B). In some implementations, this is accomplished by attaching a block of ceramic material or polymer material, or by depositing a polymer material and curing. The gap between the added supporting block and the previously deposited multilayers can be filled with a UV-curable, electron beam curable, or thermally curable polymer such as PMMA or hydrogen silsesquioxane (HSQ) resist. The HSQ resist layer deposited can be hardened by additional thermal curing to be close to a $SiO_2$ type harder material. The mechanically supportive block material can be added for subsequent planarization, as in optional block 316, or to provide support for handling, such as during a subsequent packaging process of the molecular sensor 100.

Optional block 316 includes planarizing the pairs of electrode sheets, the inner dielectric sheets, and the one or more outer dielectric sheets formed by repeating the sub-process of blocks 306 to 312. The planarizing can include, for example, CMP polishing, focused ion beam (FIB) etching, or PMMA or HSQ filling and etching back by reactive ion etch (RIE). After the repeated deposition of thin film and thick film electrodes and dielectric layers, the mechanically supportive block material added and cured in block 315, such as a $SiO_2$ material or precursor of $SiO_2$ (e.g., HSQ), can provide support during planarization.

With reference to FIG. 1B or 2B, planarization can take place along the planarization line 117 below a top surface of the protrusion 104. In other implementations, planarization can take place along the top surface of the protrusion 104 so that an exposed top surface of the electrode sheets and dielectric sheets is substantially planar with a top surface of the protrusion 104 or parallel to the substrate plane 103.

In some implementations, block 316 in FIG. 3 may be omitted such as where a sacrificial layer extended far enough over an edge of the protrusion to prevent unwanted deposition on the top of the protrusion. In such an example, removal of the sacrificial layer in block 315 may result in the exposed top surfaces of the pairs of electrode sheets without the need for planaraization.

FIG. 4A is a cross section view showing fabrication of a molecular sensor 100 by sequentially depositing tri-layer thin film device stacks using a high deposition angle according to an embodiment. FIG. 4B provides a cross section view of the molecular sensor 100 of FIG. 4A after fabrication.

The dielectric layers in FIG. 4A include the inner dielectric layers 109 and the outer dielectric layers 115. As with the protrusion 104, the inner dielectric layers 109 and the outer dielectric layers 115 can include, for example, a dielectric such as $SiO_2$, $Al_2O_3$, or MgO. As shown in FIG. 4A, a first portion of the inner dielectric layers 109 and the outer dielectric layers 115 are deposited in an orientation along the substrate plane 103 (i.e., horizontally in the example of FIG. 4A). A second portion of the inner dielectric layers 109 and the outer dielectric layers 115 are deposited in an orientation along the protrusion 104 (e.g., vertically onto the right side of the protrusion 104 in the example of FIG. 4A) to form the inner dielectric sheets 108 and the outer dielectric sheets 112, respectively. The inner dielectric sheets 108 and the outer dielectric sheets 112 are formed at an angle to the substrate plane 103.

The electrode layers in FIG. 4A include the first electrode layers 105 and the second electrode layers 113. The electrode layers can include, for example, a conductive metal such as Au, Pt, Pd, Ag, or Rh.

As shown in FIG. 4A, a first portion of the first electrode layers 105 and the second electrode layers 113 are deposited in an orientation along the substrate plane 103 (i.e., horizontally in the example of FIG. 1). A second portion of the first electrode layers 105 and the second electrode layers 113 are deposited along the protrusion 104 (e.g., vertically onto the right side of the protrusion 104 in the example of FIG. 1) to form the first electrode sheets 107 and the second electrode sheets 115, respectively. The first electrode sheets 107 and the second electrode sheets 115 are formed at an angle to the substrate plane 103.

Depositing the electrode layers and the dielectric layers at an angle to the substrate plane 103 can allow for exposing multiple pairs of electrode sheets 106. This can ordinarily allow for scalability in fabricating a large number of electrode pairs 106 by depositing many electrode and dielectric layers.

For example, a sequence of film deposition can include depositing a first conductor layer 105, followed by an inner dielectric layer 109, then followed by a deposition of a second conductor layer 113 to be paired with the first conductor layer 105, with the inner dielectric layer 109 being sandwiched by the first conductor layer 105 and second conductor layer 113. An outer dielectric layer 118 is then deposited with a sufficient thickness to separate the earlier-deposited conductor pair from a subsequent conductor pair. The deposition of conductor layer, dielectric layer, and second conductor layer can be repeated many times.

In addition to scalability, the thickness of the inner dielectric sheets 108 can be accurately controlled using standard CMOS type thin film deposition fabrication processes as with the examples of FIGS. 1C and 2C discussed above. This can ordinarily allow for a fixed and accurately controlled spacing between the two electrode sheets to facilitate a reliable and reproducible attachment of particular molecules such as certain proteins, DNAs, nucleotides, lipids, antibodies, hormones, carbohydrates, metabolites, pharmaceuticals, vitamins, neurotransmitters, enzymes, or another molecule to be analyzed. The use of standard CMOS processes to produce multi-electrode molecule sensing devices also reduces the costs typically associated with manufacturing a molecule sensor.

Each electrode sheet in FIG. 4B can have a thickness, for example, of 2 to 100 nm. Depending on design considerations such as the molecule to be analyzed, the electrode sheets and layers 107/105 and 115/113 can be deposited with a thickness of 1 to 40 nm or 5 to 15 nm. In such implementations, the inner dielectric sheets and layers 108/109 can be deposited with a similar thickness of 1 to 40 nm or 2 to 15 nm, but the outer dielectric sheets and layers 112/118 are deposited with a thickness between 50 to 2,000 nm that is at least one order of magnitude greater than the thickness of the inner dielectric sheets and layers 108/109.

The exposed first electrode sheets 107 and the exposed second electrode sheets 115 form pairs of electrode sheets 106 with a portion of the inner dielectric sheet 108 partially removed to form a groove or a gap 110. The free space of the gap 110 between the two electrode sheets can allow the molecules 10 to be more conveniently attached as shown in FIG. 4B. The molecules 10 can include, for example, a protein, DNA, nucleotide, lipid, antibody, hormone, carbohydrate, metabolite, pharmaceutical, vitamin, neurotransmitter, enzyme, or another type of molecule to be analyzed or identified.

One electrode sheet in the pair of electrode sheets 106 can serve as a source electrode and the other electrode sheet can serve as a drain electrode. In operation, a molecule 10 is attached to each electrode sheet in the pair of electrode sheets as shown in FIG. 4B to form a molecular bridge between the electrode sheets. The molecule 10 can include, for example, a protein, DNA, antibody, nucleotide, lipid, hormone, carbohydrate, metabolite, pharmaceutical, vitamin, neurotransmitter, enzyme, or another type of molecule to be identified or analyzed. The molecule 10 can then be detected or analyzed by measuring an electronic signal in the molecular sensor. In some implementations, a current is passed through the molecule 10 by forming a circuit including the first electrode sheet 107, the second electrode sheet 115, and the molecule 10. Based on the measured current, the molecule 10 can be identified or analyzed. Such an implementation can allow the molecular sensor 100 to be used for genome sequencing.

In some implementations, sensor 100 can include up to one thousand pairs of electrode sheets 106. Sensor 100 can also provide for scalability by combining multiple sensors such as sensor 100 together to obtain an even greater number of pairs of electrode sheets to simultaneously test more molecules. This scalability can ordinarily reduce the time for analyzing a large number of molecules at the same time.

As shown in FIG. 4B, each pair of electrode sheets 106 is separated by an outer dielectric sheet 112. An inner dielectric sheet 108 separates the first electrode sheet 107 and the second electrode sheet 115 in a pair of electrode sheets 106. In some implementations, the inner dielectric sheets 108 can all have approximately a first thickness (e.g., within 5%), while all the outer dielectric sheets 112 can have approximately a second thickness (e.g., within 5%) that is at least one order of magnitude greater than the first thickness. The thicker outer dielectric sheet 112 provides separation between adjacent pairs of electrode sheets 106 to reduce electrical or capacitance interference.

For example, a desired thickness of the outer dielectric sheets 112 can be at least 1 µm or at least 10 µm, while a desired thickness for the inner dielectric sheets 112 can be at most 50 nm or at most 20 nm. In some implementations, the thickness of the inner dielectric sheets 112 can be at most 10 nm. Having an accurately controlled inner dielectric layer thickness can ordinarily improve the reliable and reproducible attachment of certain molecules to the pairs of electrode sheets 106, which results in more accurate readings from the sensor 100 since it is less likely that other types of molecules inadvertently attach to the electrode sheets.

A groove or gap 110 in the inner dielectric sheet 108 can facilitate the attachment of a molecule 10 for analysis during operation. In some implementations, a partial air gap can be introduced by localized etching or by deposition with local masking to form a groove 110 in the inner dielectric sheet 108. For example, a space 5 to 15 nm deep from the exposed edge of the inner dielectric sheet 108 can be etched to produce a free spacing to facilitate the movement and attachment of certain biomolecules.

FIG. 5 is a flowchart for a manufacturing process of the molecular sensor of FIG. 4B according to an embodiment utilizing a relatively high incident angle oblique deposition. In the example process of FIG. 5, a higher incident angle oblique deposition is used than in the example process of FIG. 3 so that the electrode and dielectric layers are also deposited on the surface of the protrusion 104 opposite the substrate 102 (i.e., the top surface of the protrusion 104 in FIG. 4A). The layers are later planarized to expose the electrode sheets and dielectric sheets that have been formed at an angle to the substrate plane 103.

In comparison to the process of FIG. 3, the process of FIG. 5 generally does not include the placement of sacrificial layers or detachable shades as in block 305 of FIG. 3, or the removal of such sacrificial layers or detachable shades as in block 315 of FIG. 3. The higher deposition angle can usually prevent the unwanted deposition of layers without using sacrificial layers or detachable shades.

In block 502, a substrate such as the substrate 102 is provided defining a substrate plane. The substrate plane can be defined by being parallel with a surface of the substrate such as a top or bottom surface for supporting dielectric and electrode layers.

In block 504, a protrusion (e.g., protrusion 104) is attached to the substrate or the protrusion is formed by removing one or more portions of the substrate. As noted above, the protrusion extends or protrudes from the substrate plane at an angle, such as 90 degrees. In one example, the protrusion can be a cut-out step of an initially thicker supporting substrate. In another example, a dielectric block or other shape may be attached to a supporting substrate to form the protrusion at an angle to the substrate plane.

In block 506, a first electrode layer is deposited on the substrate using a relatively high angle of deposition, such as between 20 and 70 degrees from the substrate plane. At least a portion of the first electrode layer is deposited in an orientation along a side of the protrusion to form a first electrode sheet (e.g., first electrode sheet 107 in FIG. 4A) at the angle to the substrate plane. In other implementations, an initial dielectric layer may be deposited before the first electrode layer is deposited in block 506.

In the example process of FIG. 5, an inner dielectric layer is deposited in block 508 on the first electrode layer deposited in block 506. As shown in the example of FIG. 4A, at least a portion of the inner dielectric layer is deposited in the orientation along the protrusion 104 to form the inner dielectric sheet 108 at the angle to the substrate plane 103. As with the first electrode layer deposited in block 506, oblique incident deposition can be used to deposit the inner dielectric layer at the angle to the substrate plane. Standard CMOS processes such as oblique incident deposition can ordinarily allow for the inner dielectric layer to be deposited with an accurate and repeatable thickness.

In some implementations, a thin adhesion enhancing layer may be deposited on the first electrode layer before and/or after depositing the inner dielectric layer to improve adhesion of the layers. In one example, a 1 to 5 nm thick film material is deposited at the interface using a material such as Ti, Cr, Al, Zr, Mo, Nb, Ta, or Hf.

In block 510, a second electrode layer is deposited on the inner dielectric layer to form a second electrode sheet (e.g., second electrode sheet 115 in FIG. 4A) at the angle to the substrate plane, using, for example, oblique incident deposition. The first electrode sheet and the second electrode sheet form a pair of electrode sheets with the inner dielectric sheet between the first electrode sheet and the second electrode sheet.

In block 512, an outer dielectric layer is deposited on the second electrode layer to form an outer dielectric sheet at an angle to the substrate plane. With reference to the example in FIG. 4B, the outer dielectric layer is deposited on the second electrode layer to form the outer dielectric sheet 112 at an angle to the substrate plane 103. In some implementations, the outer dielectric layer may have a different thickness if it is a final outer dielectric layer to, for example, facilitate packaging of the sensor in a larger array of sensors or to provide a greater exterior insulation.

In block 514, it is determined whether a final number of pairs of electrode sheets has been reached. In some implementations, the final number of pairs of electrode sheets may be as few as two pairs of electrode sheets. In this regard, the sub-process of blocks 506 to 512 is repeated at least once to provide for at least two pairs of electrode sheets. In some implementations, the final number of pairs of electrode sheets may be as large as several thousand pairs of electrode sheets for example. The final number of pairs of electrode sheets may depend on the design considerations for the sensor being manufactured, such as a desired testing speed, a type of molecule to be analyzed, or a desired footprint for the sensor.

If the final number of pairs of electrode sheets has not been reached in block 514, the process returns to block 506 to deposit another first electrode layer in an orientation along a side of the protrusion to form another first electrode sheet at an angle to the substrate plane.

On the other hand, if the final number of pairs of electrode sheets has been reached in block 514, the process proceeds to block 515 to add at least one mechanically supportive block material with a gap-filling curable polymer. A mechanically supportive block material may be attached adjacent the deposited multilayer stack (e.g., block 123 added to the right of the deposited layers shown in FIG. 4A). In some implementations, this is accomplished by attaching a block of ceramic material or polymer material, or by depositing a polymer material and curing. The gap between the added supporting block and the previously deposited multilayers can be filled with a UV-curable, electron beam curable, or thermally curable polymer such as PMMA or HSQ resist. The HSQ resist layer deposited can be hardened by additional thermal curing to be close to a $SiO_2$ type harder material. The mechanically supportive block material is added for subsequent planarization, as in block 516, or to provide support for handling, such as during a subsequent packaging process of the molecular sensor 100.

Block 516 includes planarizing the pairs of electrode sheets, the inner dielectric sheets, and the one or more outer dielectric sheets formed by repeating the sub-process of blocks 506 to 512. The planarizing can include, for example, CMP polishing, FIB etching, or PMMA or HSQ filling and etching back by RIE. After the repeated deposition of thin film and thick film electrodes and dielectric layers, the mechanically supportive block material added and cured in block 515, such as a $SiO_2$ material or precursor of $SiO_2$ (e.g., HSQ), can provide support during planarization. With reference to FIG. 4A, planarization can take place along the planarization line 117, which is along the top surface of the protrusion 104 so that an exposed top surface of the electrode sheets and dielectric sheets is substantially planar with a top surface of the protrusion 104 or parallel to the substrate plane 103. In other implementations, the planarization can take place below the top surface of the protrusion 104 to expose the pairs of electrode sheets.

Figure 6:
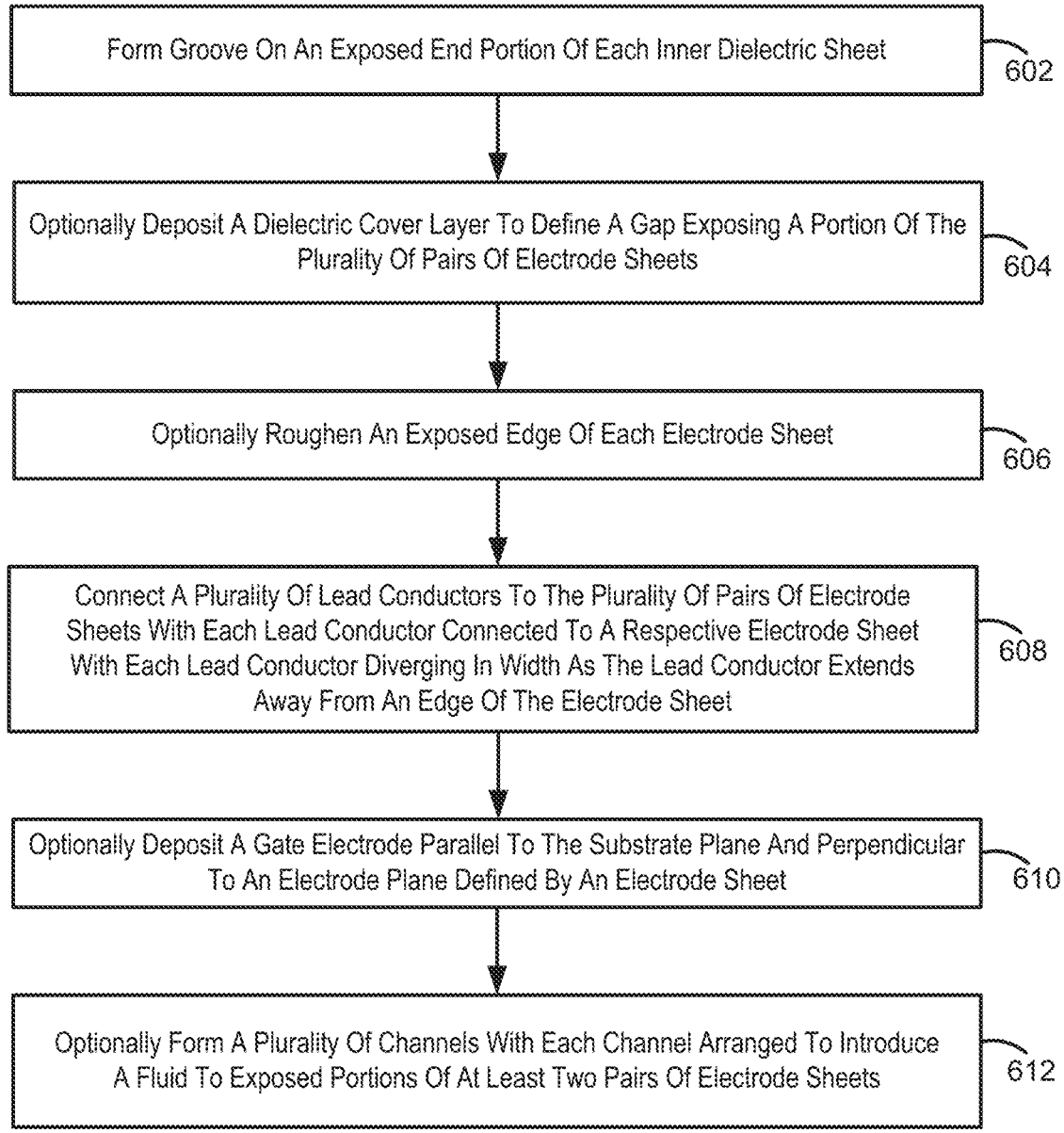
FIG. 6 is a flowchart for an additional manufacturing process according to an embodiment.

FIG. 6 is a flowchart for a manufacturing process that can follow the manufacturing process of either FIG. 3 or FIG. 5 according to an embodiment. In block 602, a groove is formed on an exposed end portion of each inner dielectric sheet. As noted above, the groove or gap can be formed by etching the inner dielectric sheet using an etching process such as RIE, sputter etch, or a chemical etch like HF etch. In one implementation, an electrical, capacitance, or optical measurement such as a voltage, electrical resistance, or optical penetration or interference can be measured between the first electrode sheet and the second electrode sheet to form the groove to a particular depth. In such an implementation, etching can be performed until the measurement reaches a threshold value corresponding to the desired depth of the groove. Further removal of the inner dielectric sheet is then stopped based on the electrical measurement reaching the threshold value.

In block 604, a dielectric cover layer is optionally deposited to define a gap exposing a portion of the plurality of pairs of electrode sheets. In some implementations, a mask line is deposited across an end portion of the pairs of electrode sheets and the dielectric cover layer is deposited on at least one side of the mask line to cover a remaining exposed portion of the pairs of electrode sheets not covered by the mask line. The mask line is then removed so that the dielectric cover layer defines a gap exposing the end portion of the pairs of electrode sheets. In other embodiments, block 604 may be omitted such that the deposition of the mask line and the dielectric cover layer is not performed.

By limiting the exposed area of the pairs of electrode sheets, it is ordinarily possible to improve the accuracy of the sensor because the gap can prevent more than one molecule from attaching to the electrode sheets in each pair of electrode sheets. When more than one molecule attaches, the readings for the pair of electrode sheets are affected. In the case where a current is measured between the electrode sheets via the molecule, the attachment of multiple molecules between the electrode sheets can lower the current measured across the electrode plates and lead to an inaccurate measurement. In some implementations, the gap defined by the dielectric cover layer is between approximately 2 to 40 nanometers depending on the type of molecule to be attached. In some implementations, the width of the gap can be between 5 and 15 nm wide.

Figure 7A:
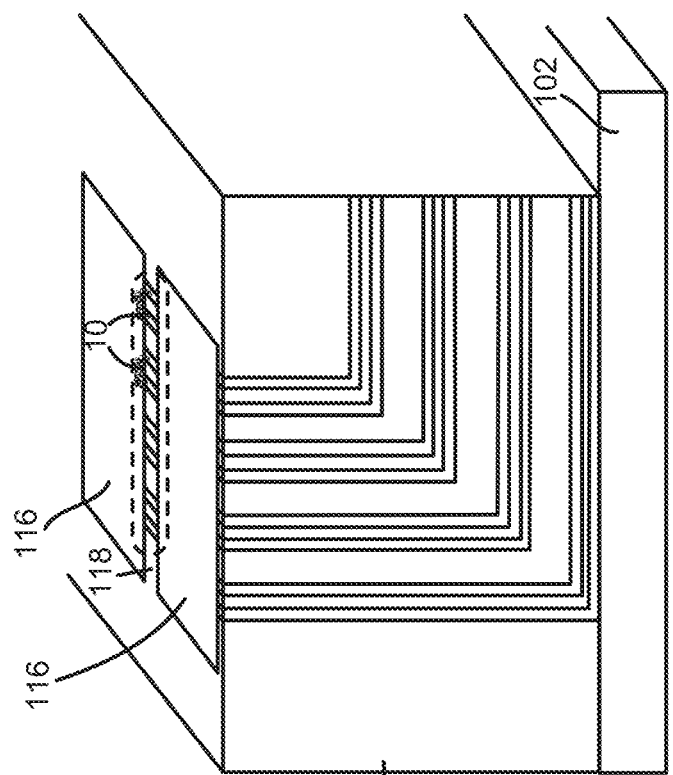
FIG. 7A is a cross section of a molecular sensor showing the deposition of a mask line during the manufacturing process of FIG. 6.
Figure 7B:
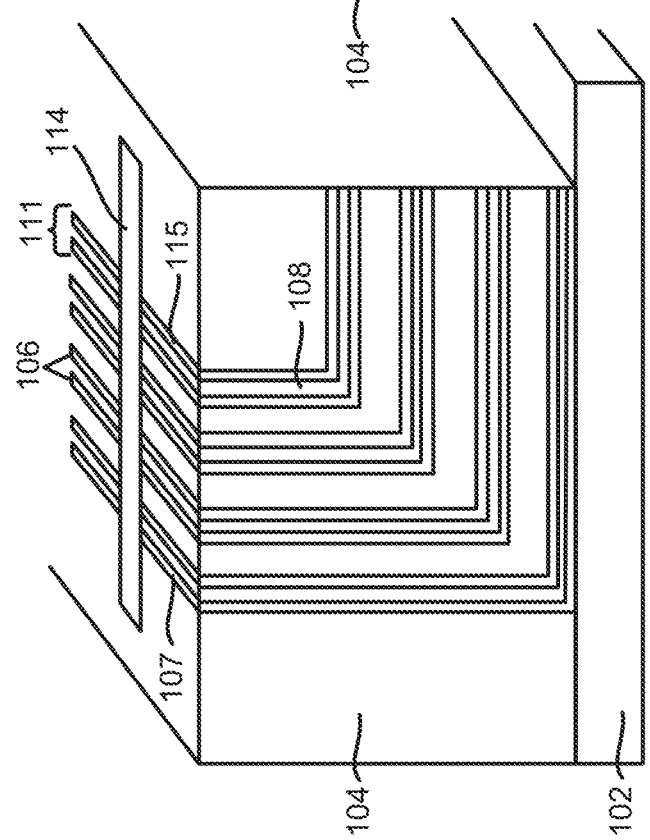
FIG. 7B is a cross section of the molecular sensor of FIG. 7A after depositing a dielectric cover layer and removing the mask line of FIG. 7A.

FIG. 7A is a cross section showing the deposition of a mask line 114 across pairs of electrode sheets 106. The mask line 114 can be deposited using, for example, an HSQ resist. As shown in FIG. 7B, a dielectric cover layer 116 is deposited on both sides of the mask line 114. The dielectric cover layer 116 can include, for example, a $SiO_2$ layer. After removal of the mask line 114, only the end portion of the electrode sheet pairs in the gap 118 are exposed for attaching a single molecule 10 to each exposed pair of electrode sheets. In other implementations, the gap 118 may be formed by using a patterning process such as e-beam lithography or nano-imprinting, and etching an unmasked region to form the gap 118. In some examples, the gap 118 can have a width between 2 to 40 nm or 5 to 15 nm to facilitate the attachment of a single molecule at each pair of electrode sheets 106.

Figure 8:
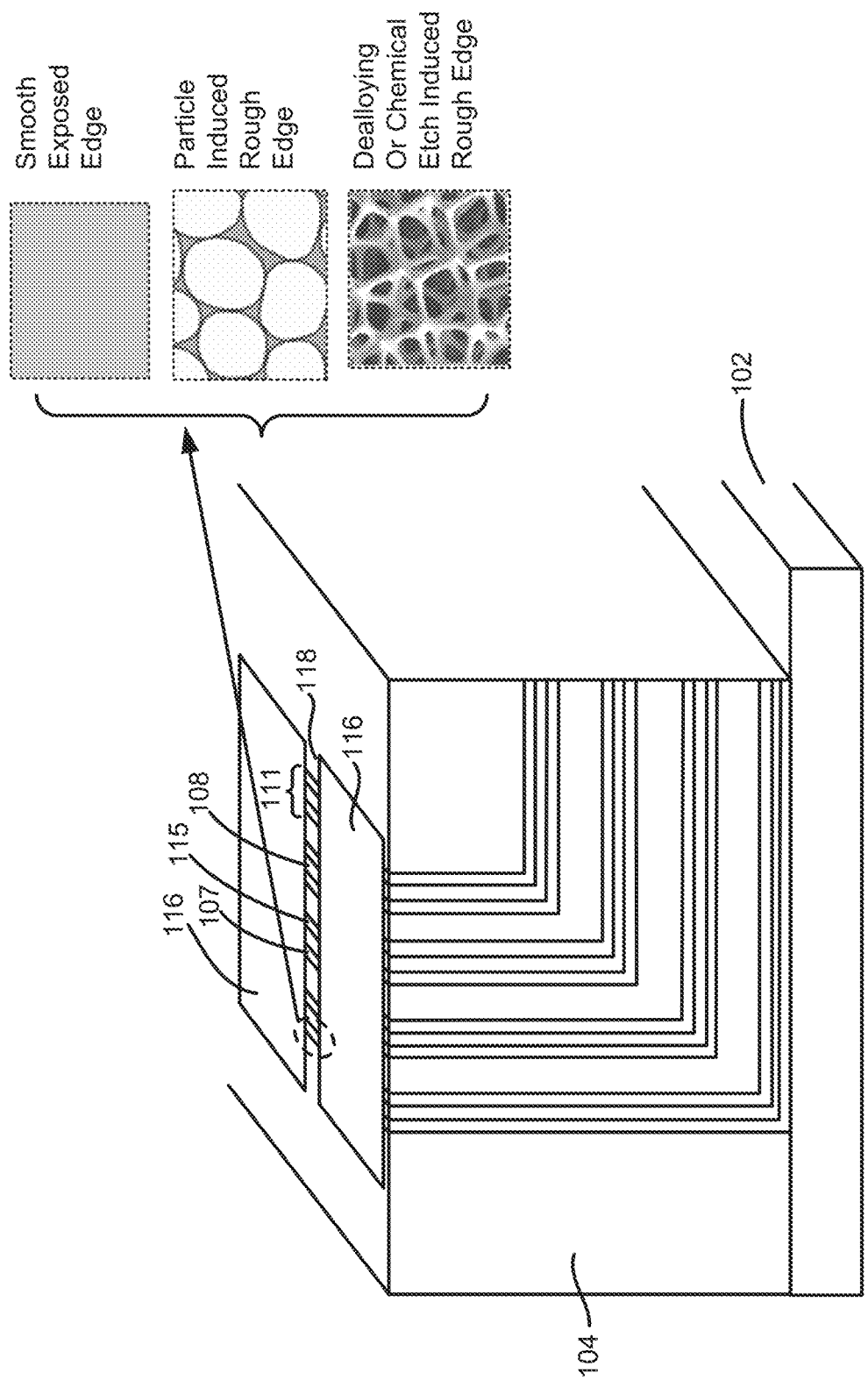
FIG. 8 is a cross section of the molecular sensor of FIG. 7B illustrating the roughening of an exposed portion of electrode sheets according to an embodiment.

Returning to the manufacturing process of FIG. 6, an exposed edge of each electrode sheet can be roughened in block 606 to improve the attachment of a molecule to the edge of the electrode sheet. FIG. 8 illustrates the roughening of an exposed portion of the first electrode sheets 107 and the second electrode sheets 115 according to an embodiment. The exposed portions of the electrode sheets in gap 118 may be roughened by, for example, dealloying of a base alloy (e.g., dealloying an Au—Ag alloy), mechanical sand blasting, ion bombardment, electron bombardment, ion implantation, chemical etching, or electrochemical etching. The surface roughening may include a feature size of 0.5 to 20 nm. In some examples, the surface roughening feature size can be between 1 to 10 nm, or between 1 to 5 nm.

The roughening of the exposed edges of the electrode sheets ordinarily provides for easier and more secure molecular attachment due to the higher surface area of the roughened surface. Other processes may be performed on the exposed edges of the electrode sheets to improve attachment of the analyte molecule. Examples of such processes can include the nano-tip or nano-pillar conductive islands discussed in U.S. Provisional Application No. 62/288,364, entitled "Massively Parallel DNA Sequencing Apparatus Comprising Strongly Adhered Conductor Nanotips and Nanoparticles, Method of Fabrication, and Applications Thereof", and filed by the present Applicant on Jan. 28, 2016, the entire contents of which are hereby incorporated by reference. Other examples of improving the attachment of the analyte molecule, such as using conductive islands with reduced contact resistance, can be found in U.S. Provisional Application No. 62/293,239, entitled "Electronic, Label-Free DNA and Genome Sequencing Apparatus, Method of Fabrication, and Applications Thereof", and filed by the present Applicant on Feb. 9, 2016, the entire contents of which are hereby incorporated by reference.

Figure 9:
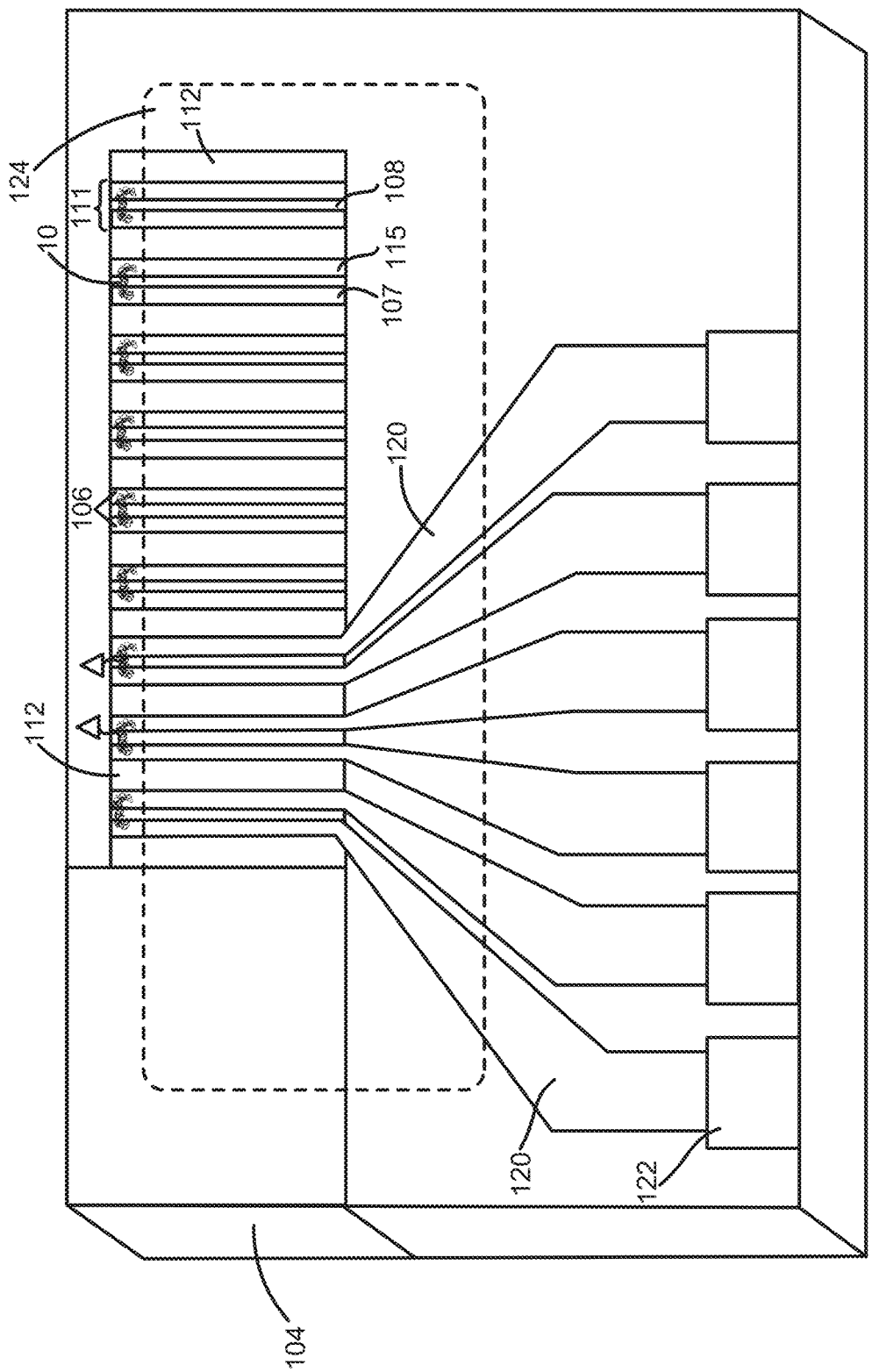
FIG. 9 is a top view of a molecular sensor with diverging lead conductors according to an embodiment.

Returning to the process of FIG. 6, a plurality of lead conductors are connected to the plurality of electrode sheets in block 608, with each lead conductor connected to a respective electrode sheet. As shown in the example of FIG. 9, the lead conductors 120 diverge in width as the lead conductor extends away from an edge of the electrode sheet toward the contact 122. The lead conductors can be made of a conductive material such as gold for carrying a test signal from the electrode sheets. In some implementations, the thickness of the electrode sheets can be as small as only 10 nm. The lead conductors may then fan out from a width of approximately 10 nm to a scale of micrometers to allow for soldering at the contacts 122. The contacts 122 can include a contact pad array for circuit packaging, solder bonding, or wire bonding.

As shown in FIG. 9, a dielectric cover layer 124 may also be applied so that only a portion of the pairs of electrode sheets 106 are exposed. The dielectric cover layer may also cover a portion of the lead conductors 120. In some implementations, the dielectric cover layer 124 can have a thickness of 1 to 20 nm or 1 to 10 nm of a dielectric material such as $SiO_2$, $Al_2O_3$, MgO, PMMA, or polydimethylsiloxane (PDMS). Similar to the dielectric cover layer discussed above for block 604, the dielectric cover layer 124 in FIG. 9 can improve the accuracy of readings by facilitating the attachment of only one molecule per pair of electrode sheets 106. In this regard, only one molecule 10 is shown attached to each pair of electrode sheets 106.

In some implementations, multiple molecular sensors such as the block shown in FIG. 9 may be joined together for scalability. For example, 1 to 1,000 blocks may be joined together, with each block including 100 to 5,000 pairs of electrode sheets 106. The joined blocks may then be planarized to the same height using, for example, CMP polishing, FIB etching, PMMA or HSQ filling and etching back by RIE. This can also allow for the placement of electrical circuits or components on the joined blocks.

Figure 10:
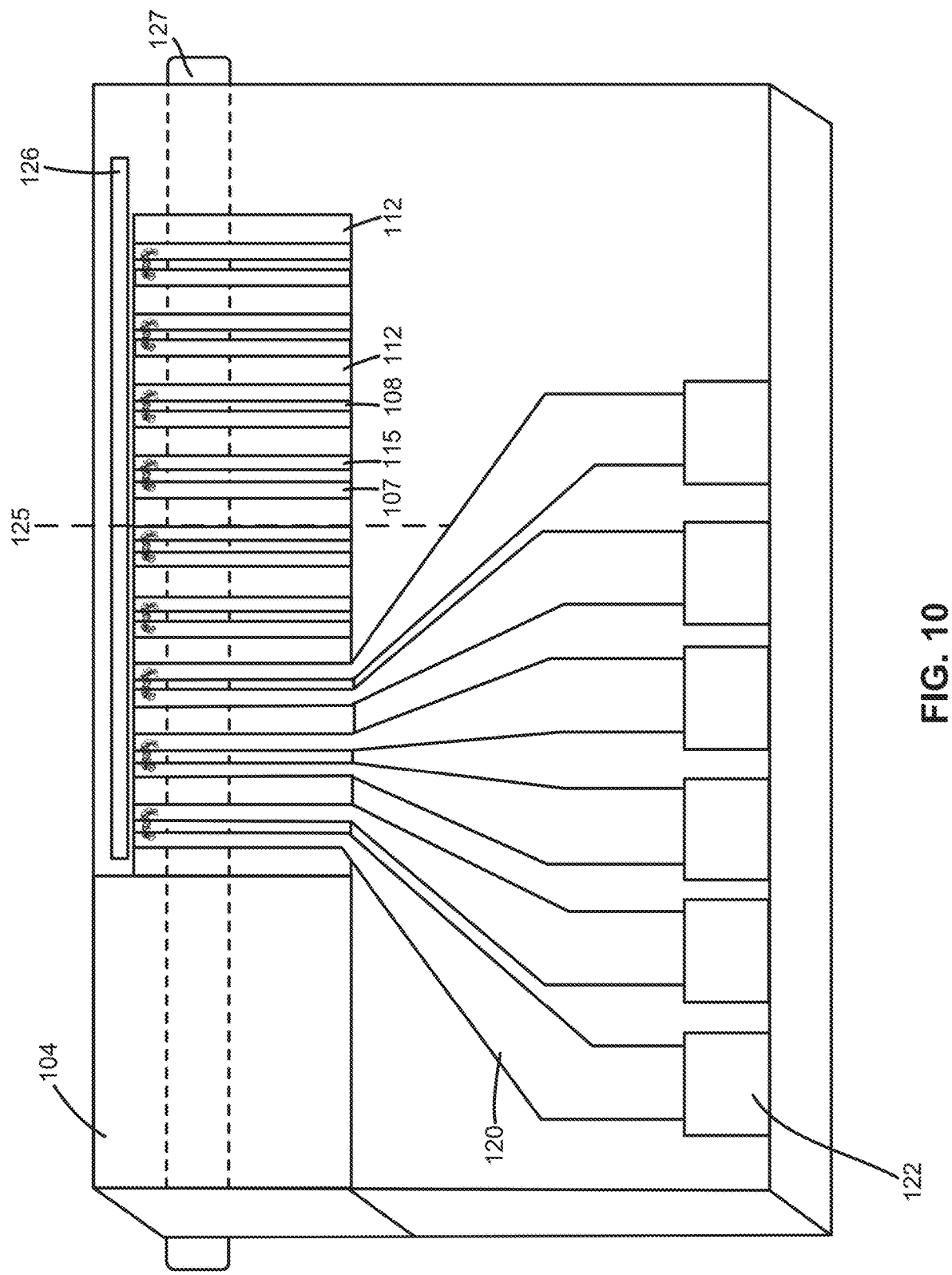
FIG. 10 is a top view of the molecular sensor of FIG. 9 with a gate electrode according to an embodiment.

In block 610 of FIG. 6, a gate electrode is optionally deposited parallel to the substrate plane and perpendicular to an electrode plane defined by an electrode sheet. The gate electrode can include, for example, a Si or metallic electrode placed on a side of the substrate opposite the electrode sheets or near a front portion of the electrode sheets on the same side of the substrate as the electrode sheets. FIG. 10 discussed below provides examples showing the placement of electrode gates in these locations.

As shown in FIG. 10, the electrode gate 126 is located near the front portion of the electrode sheets and extends along a length of the electrode sheets in a direction perpendicular to the electrode sheet plane 125 defined by one of the electrode sheets. The electrode gate 127 is located on the backside of the substrate 102 extending across the substrate 102 in a direction perpendicular to the electrode sheet plane 125.

The addition of an electrode gate can ordinarily improve the accuracy of readings from the pairs of electrode sheets by imposing an electric field to regulate the charge carriers between the first electrode sheet and the second electrode sheet, which serve as source and drain electrodes. An electrode gate can be especially helpful in implementations where the electrode sheets include a semiconductor. On the other hand, some implementations may not include an electrode gate such that block 608 may be omitted from the process of FIG. 6.

In some implementations, the arrangement of FIG. 10 can include one or more dielectric cover layers similar to the dielectric cover layer 124 in FIG. 9 discussed above. The dielectric cover layer or layers can be deposited at an angle to or perpendicular to the electrode sheets on the surface of the planarized structure to expose only a narrow gap portion of the electrode sheets for molecular sensing.

Figure 11:
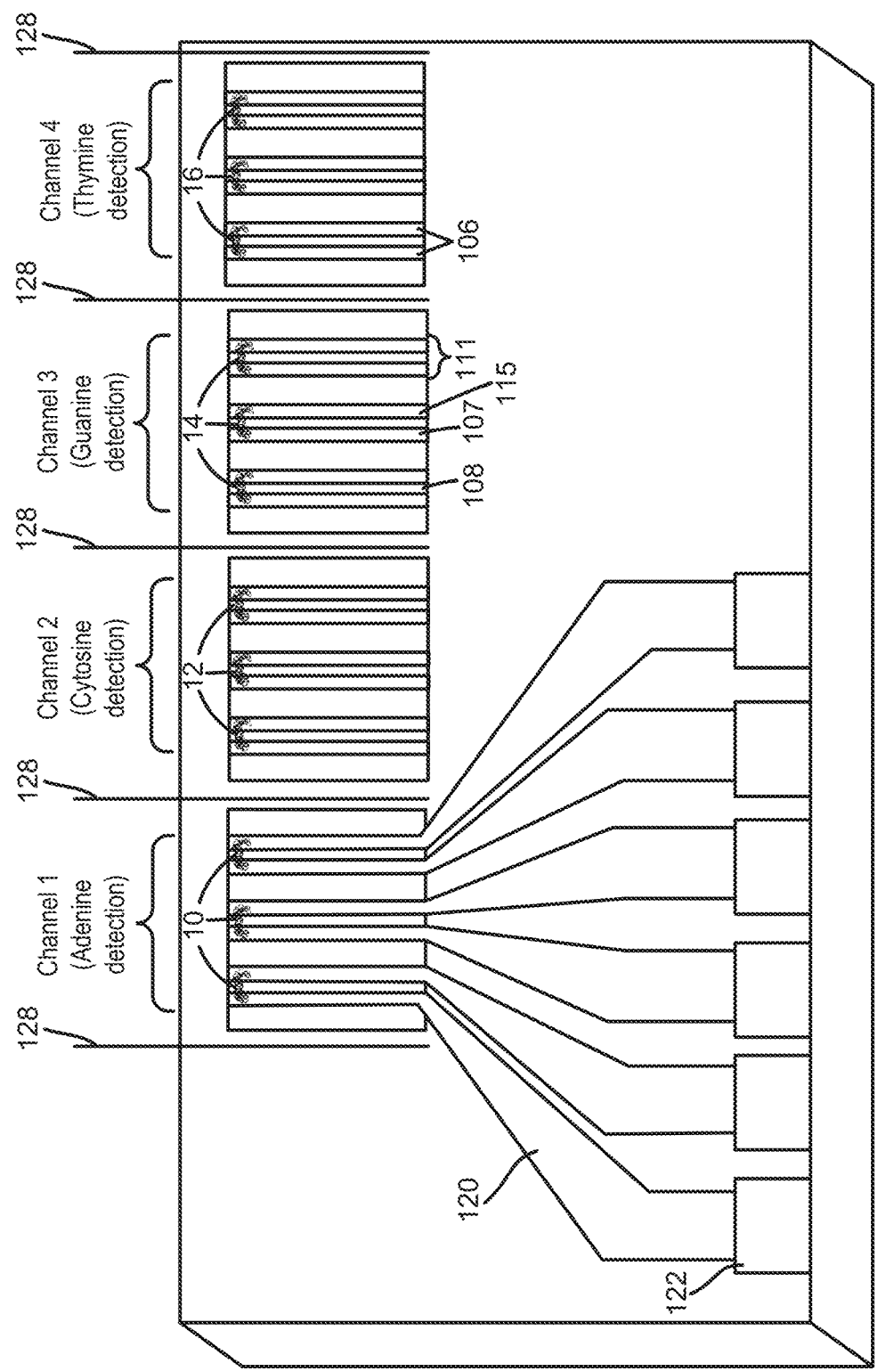
FIG. 11 is a top view of a molecular sensor with channels for introducing a fluid to pairs of electrode sheets according to an embodiment.

In block 612 of FIG. 6, a plurality of channels is optionally formed with each channel arranged to introduce a fluid to the exposed portions of the electrode sheets. Each channel includes at least two pairs of electrode sheets. As shown in the example of FIG. 11, each channel can be formed by adding a wall 128 between a group of pairs of electrode sheets. A fluid such as a gas or liquid containing the molecules to be tested can then be introduced into the channel so that multiple pairs of electrodes can be used to test the molecules in the fluid. In the example of FIG. 11, each channel is loaded with a fluid containing a different DNA nucleobase for detection via the pairs of electrode sheets 106 in the channel.

The arrangement shown in FIG. 11 can ordinarily allow for error correction or compensation by loading the same fluid to be tested (e.g., a fluid with molecules 10, 12, 14, or 16 in FIG. 11) across multiple pairs of electrode sheets 106 and using the different measurements for the different pairs of electrode sheets to average out any error and/or eliminate a measurement that deviates by more than a threshold. Although three pairs of electrode sheets are shown per channel in the example of FIG. 11, a different number of pairs can be used in different implementations, such as ten or twenty pairs of electrode sheets per channel.

In some implementations, the arrangement shown in FIG. 11 can include one or more dielectric cover layers similar to the dielectric cover layer 124 in FIG. 9 discussed above. The dielectric cover layer or layers can be deposited at an angle to or perpendicular to the electrode sheets on the surface of the planarized structure to expose only a narrow gap portion of the electrode sheets for molecular sensing.

Figure 12:
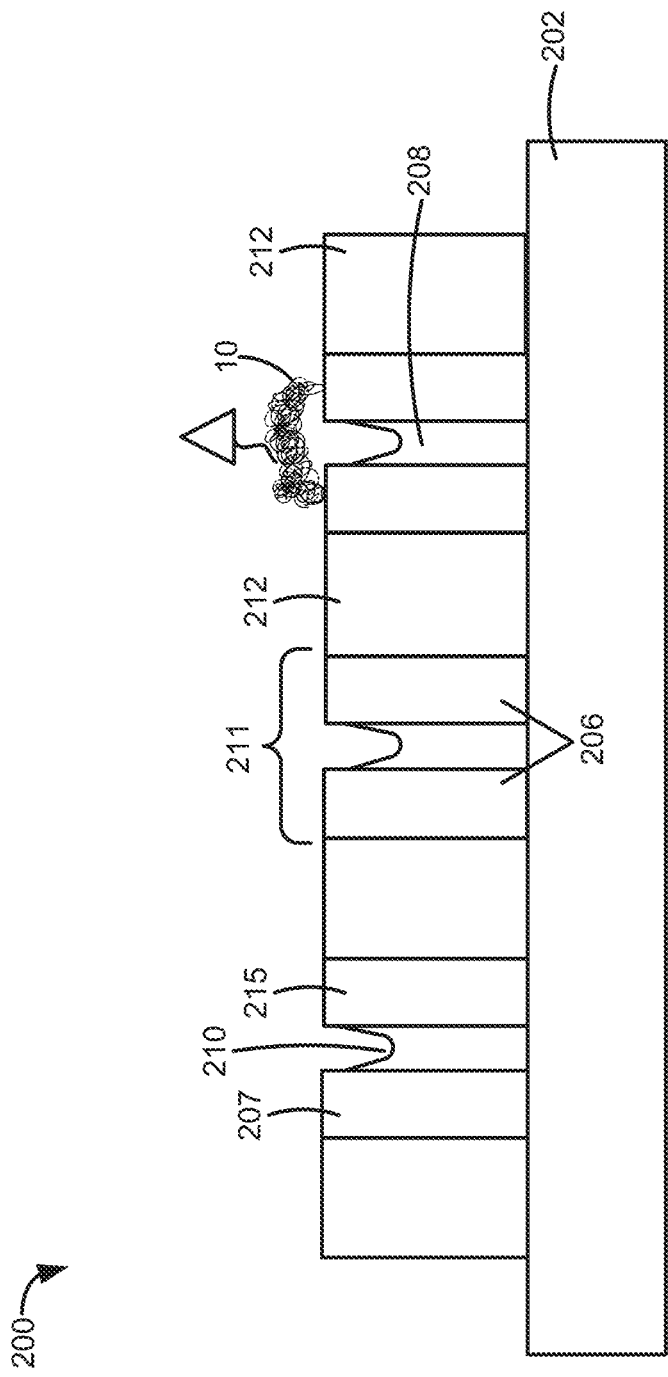
FIG. 12 depicts a molecular sensor manufactured by forming a stack of layers and slicing through the stack according to an embodiment.

FIG. 12 provides a side view of a molecular sensor 200 according to an embodiment where the molecular sensor is manufactured by forming a stack of electrode and dielectric layers and slicing through the stack. As shown in FIG. 12, sensor 200 includes a supporting substrate 202 that can include, for example, $SiO_2$ or Si with an $SiO_2$ coating. In the example of FIG. 12, the pairs of electrode sheets 206, inner dielectric sheets 208, and outer dielectric sheets 212 are at a perpendicular angle to the substrate 202 so that the electrode sheets are in a vertical or near-vertical configuration. Other implementations can include a tilted angle orientation of up to about a 60 degree tilting of the electrode sheets from a vertical alignment, but preferably with less than 20 degrees of tilting. In such implementations, the sheets may extend from the substrate 202 at an angle, such as a 45 or 60 degree angle.

The inner dielectric sheets 108 and the outer dielectric sheets 212 can include, for example, a dielectric such as $SiO_2$, $Al_2O_3$, or MgO. The electrode sheets 207 and 215 can include, for example, a conductive metal such as Au, Pt, Pd, Ag, or Rh.

As discussed in more detail below with reference to FIG. 13, the molecular sensor 200 is formed by slicing a stack of dielectric and electrode layers into a plurality of chips, and attaching the plurality of chips to a substrate such as substrate 202 so that a desirably aligned structure of electrode pairs and dielectric spacers is obtained. This can ordinarily allow for fabricating a large number of electrode sheet pairs 206 by attaching multiple chips and/or using multiple layers in forming the stack.

The alignment of layers at an angle to the substrate 202, as opposed to parallel to the substrate 202, improves control of the degree of etching of the inner dielectric sheets 208. This can allow for a more accurate and reproducible cavity structure or grooves 210 to provide for easier attachment of a single molecule for analysis when DNA, a nucleotide, or other analyte is attached. In addition, and as with the molecular sensor 100 discussed above, the thickness of the inner dielectric layers 208 can be accurately controlled using standard CMOS fabrication processes to facilitate the attachment of particular molecules such as proteins, DNAs, nucleotides or another molecule to be analyzed. The use of standard CMOS processes to produce multi-electrode molecule sensing devices also reduces the costs typically associated with manufacturing a molecule sensor.

The exposed first electrode sheets 207 and the exposed second electrode sheets 215 form pairs of electrode sheets 206 for attaching molecules 10. One electrode sheet in the pair of electrode sheets 206 can serve as a source electrode and the other electrode sheet can serve as a drain electrode. In operation, a molecule 10 is attached to each electrode sheet in the pair of electrode sheets as shown in FIG. 12 to form a molecular bridge. The molecule 10 can include, for example, a protein, DNA, antibody, nucleotide, lipid, hormone, carbohydrate, metabolite, pharmaceutical, vitamin, neurotransmitter, enzyme, or another type of molecule to be identified or analyzed. The molecule 10 can then be detected or analyzed by measuring an electronic signal in the molecular sensor. In some implementations, a current can be passed through the molecule 10 by forming a circuit including the first electrode sheet 207, the second electrode sheet 215, and the molecule 10. Based on the measured current, the molecule 10 can be identified or analyzed. Such an implementation can allow the molecular sensor 100 to be used for genome sequencing.

In some implementations, sensor 200 can include up to one thousand pairs of electrode sheets 206. Sensor 200 can also provide for scalability by combining multiple sensors such as sensor 200 together to obtain an even greater number of pairs of electrodes to simultaneously test more molecules. This scalability can ordinarily reduce the time for analyzing a large number of molecules at the same time.

As shown in FIG. 12, each pair of electrode sheets 206 is separated by an outer dielectric sheet 212. An inner dielectric sheet 208 separates the first electrode sheet 207 and the second electrode sheet 215 in a pair of electrode sheets 206. In some implementations, the inner dielectric sheets 208 can all have approximately a first thickness (e.g., within 5%), while all the outer dielectric sheets 212 can have approximately a second thickness (e.g., within 5%) that is at least one order of magnitude greater than the first thickness. The thicker outer dielectric sheet 212 provides separation between adjacent pairs of electrode sheets 206 to reduce electrical, inductive, or capacitance interference.

In some implementations, a desired thickness of the outer dielectric sheets is at least 0.5 µm, and preferably at least 1 µm or at least 10 µm, while the inner dielectric sheets are at most 50 nm, 20 nm, or 10 nm thick. As noted above, an accurately controlled inner dielectric sheet thickness can ordinarily improve the reliable and reproducible attachment of certain molecules to the pairs of electrode sheets 206. This in turn can result in more accurate readings from the sensor 200 since it is less likely that other types of molecules inadvertently attach to the electrode sheets.

A groove or gap 210 in the inner dielectric sheet 208 can facilitate the attachment of a molecule 10 for analysis during operation. In some implementations, a partial air gap can be introduced by localized etching or by deposition with local masking to form a groove 210 in the inner dielectric sheet 208. For example, a 5 to 15 nm space can be etched to facilitate the attachment of certain biomolecules.

Figure 13:
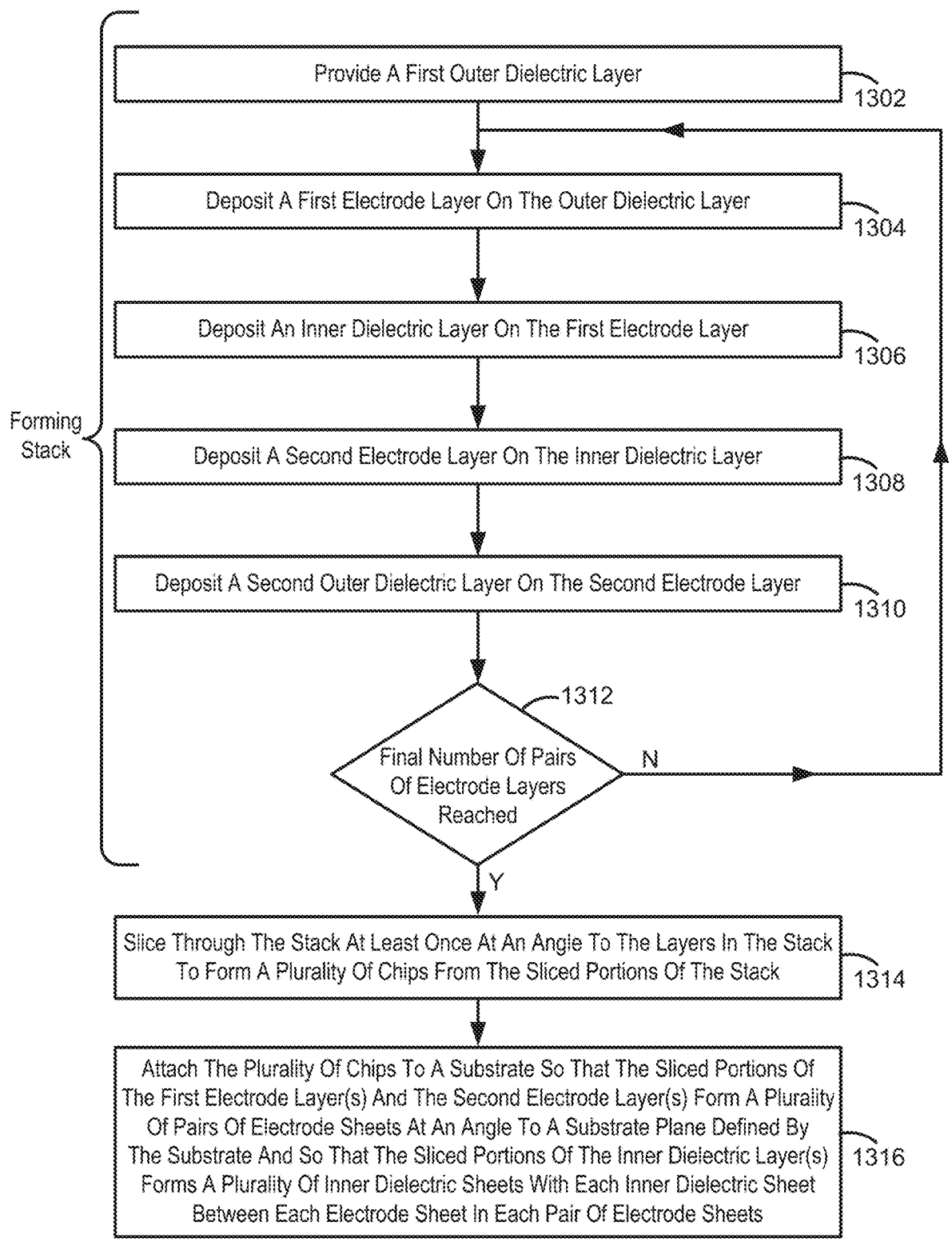
FIG. 13 is a flowchart for a manufacturing process of the molecular sensor of FIG. 12 according to an embodiment.

FIG. 13 is a flowchart for a manufacturing process of the molecular sensor 200 of FIG. 12 according to another embodiment. As shown in FIG. 13, blocks 1302 to 1312 are collectively performed to form a stack that is later sliced in block 1314 to form multiple chips that are attached to a substrate in block 1316.

In block 1302, a first outer dielectric layer is provided, and a first electrode layer is deposited on the first outer dielectric layer in block 1304. The first electrode layer can be deposited using a standard CMOS deposition technique. In some implementations, the outer dielectric layer may have a different thickness than other outer dielectric layers to, for example, facilitate packaging of the sensor in a larger array of sensors or to provide a greater exterior insulation. In other implementations, the thickness of the first outer dielectric layer may be the same as other outer dielectric layers located between electrode sheets in the pairs of electrode sheets.

In block 1306, an inner dielectric layer is deposited on the first electrode layer. A second electrode layer is deposited on the inner dielectric layer in block 1308 to form a pair of electrode layers with the inner dielectric layer between the first and second electrode layer. In block 1310, a second outer dielectric layer is deposited on the second electrode layer deposited in block 1308. The thickness of the second outer dielectric layer may be the same or may differ from the thickness of the first outer dielectric layer provided in block 1302.

In block 1312, it is determined whether a final number of pairs of electrode layers has been reached for the stack. If so, the process proceeds to block 1314 to slice through the stack at least once at an angle to the layers in the stack to form a plurality of chips from the sliced portions of the stack. On the other hand, if it is determined that the final number of pairs of electrode layers has not been reached in block 1312, the process returns to block 1304 to deposit another first electrode layer on the second outer dielectric layer deposited in block 1310. The depositing of the first electrode layer, the inner dielectric layer, the second electrode layer, and the second outer dielectric layer in blocks 1304 to 1310 repeats until a final number of pairs of electrode layers has been reached in block 1312.

Figure 14:
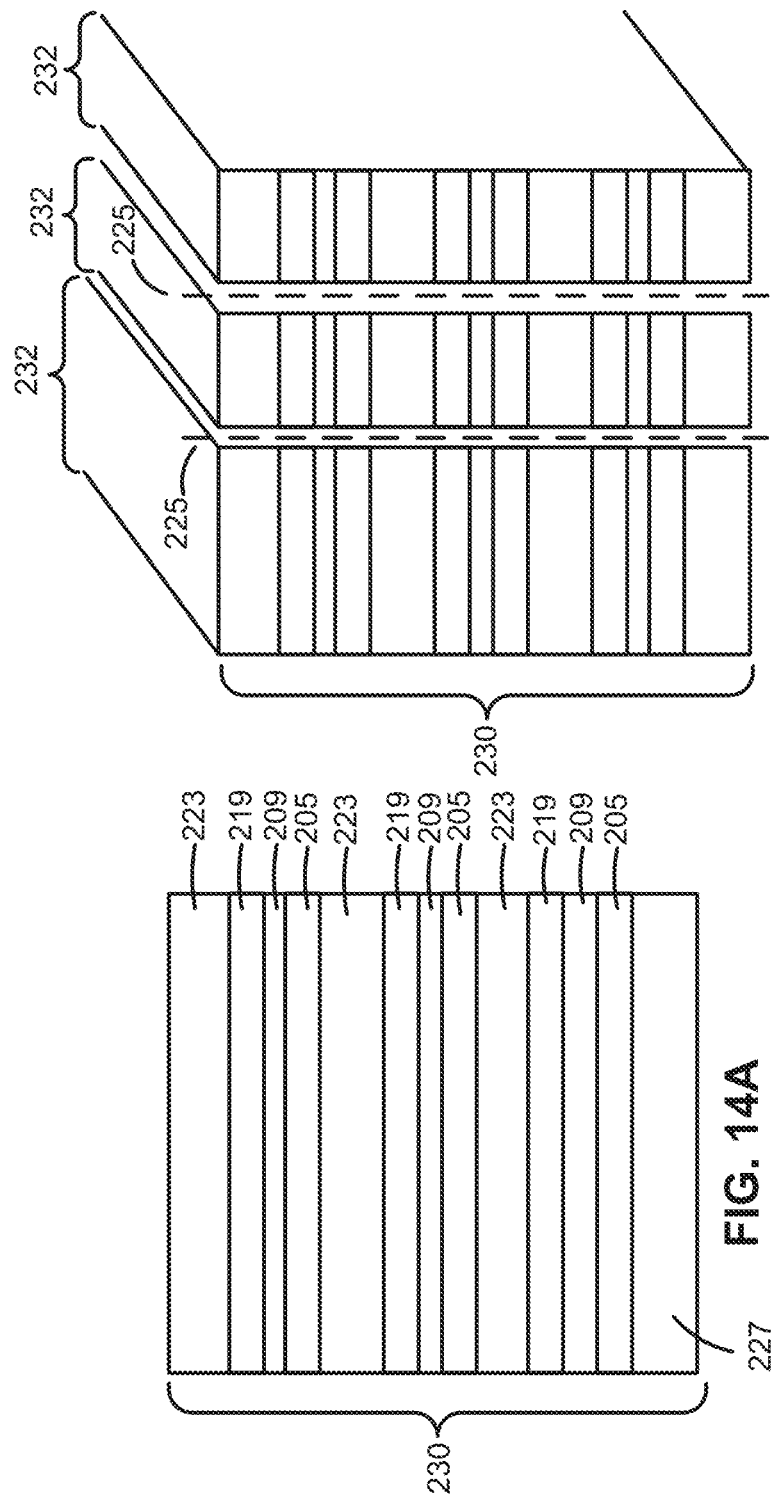
FIG. 14A is a cross section of a stack of layers during the manufacturing process of FIG. 13.
FIG. 14B illustrates the slicing of the stack of FIG. 14A to form chips during the manufacturing process of FIG. 13.
FIG. 14C is a cross section view showing the placement of a chip from FIG. 14B on a substrate during the manufacturing process of FIG. 13.

FIG. 14A provides an example of a stack 230 formed by performing blocks 1302 to 1312 in the manufacturing process of FIG. 13. As shown in FIG. 14A, a first outer dielectric layer 227 is provided and a first electrode layer 205 is deposited on the first outer dielectric layer 227. An inner dielectric layer 209 is deposited on the first electrode layer 205 and a second electrode layer 219 is deposited on the inner dielectric layer 209. A second outer dielectric layer 223 is deposited on the second electrode layer 219. This pattern of depositing a first electrode layer 205, an inner dielectric layer 209, a second electrode layer 219, and a second dielectric layer 223 is repeated two more times in the example of FIG. 14A to result in a stack 230 with three pairs of electrode layers.

In some implementations, a thin adhesion enhancing layer may be deposited at the interfaces between the electrode layers and the inner dielectric layers to improve the adhesion of the layers. In one example, a 1 to 5 nm thick film material is deposited at the interface using a material such as Ti, Cr, Al, Zr. Mo, Nb, Ta, or Hf.

In some implementations, the electrode layers 205 and 219 are deposited with a thickness of 1 to 40 nm or 5 to 15 nm. In such implementations, the inner dielectric layers 209 can be deposited with a similar thickness of 1 to 40 nm or 2 to 15 nm, but the outer dielectric layers 223 are deposited with a thickness between 50 to 2,000 nm that is at least one order of magnitude greater than the thickness of the inner dielectric layers 209.

Returning to the process of FIG. 13, the stack formed in blocks 1302 to 1312, is sliced through at least once in block 1314 to form a plurality of chips from the sliced portions of the stack. The stack is sliced at an angle to the layers in the stack to expose a cross section of the layers deposited in the stack. In some implementations, the stack is sliced at a 90 degree angle to the layers in the stack. In other implementations, the stack may be sliced at a different angle to the layers in the stack.

FIG. 14B illustrates the slicing of the stack 230 of FIG. 14A to form a plurality of chips 232 including at least one pair of electrode sheets. As shown in FIG. 14B, the stack 230 is sliced along planes 225 to form three chips 232, which may have the same thickness/height or different thicknesses/heights.

In block 1316 of FIG. 13, the plurality of chips are attached to a substrate so that the sliced portions of the first electrode layer or layers and the second electrode layer or layers form a plurality of pairs of electrode sheets at an angle to a substrate plane defined by the substrate. In addition, the sliced portions of the inner dielectric layer or layers form a plurality of inner dielectric sheets with each inner dielectric sheet between each electrode sheet in each pair of electrode sheets.

The manufacturing process of FIG. 13 may be followed with one or more additional processes, such as with the performance of one or blocks in FIG. 6 discussed above. Such additional processes can include, for example, forming a groove on an exposed end portion of each inner dielectric sheet (e.g., block 602 in FIG. 6), defining a gap in a cover layer (e.g., block 604), roughening an exposed edge of each electrode sheet (e.g., block 606), depositing a gate electrode (e.g., block 608), forming a plurality of channels (e.g., block 610), and connecting lead conductors (e.g., block 612).

FIG. 14C is a cross section view showing the placement of a chip 232 from FIG. 14B on a substrate 202 during the manufacturing process of FIG. 13. As shown in FIG. 14C, a chip 232 has been rotated 90 degrees and attached to substrate 202 to reveal multiple exposed electrode sheet pairs 206. Each pair of electrode sheets 206 includes a first electrode sheet 207 and a second electrode sheet 215, with an inner dielectric sheet 208 sandwiched between the electrode sheets. Outer dielectric sheets 212 are provided between each pair of electrode sheets 206 and on the ends of the chip 232. In some implementations the first or the last outer dielectric sheets 212 may have a different thickness than other outer dielectric sheets.

Figure 15:
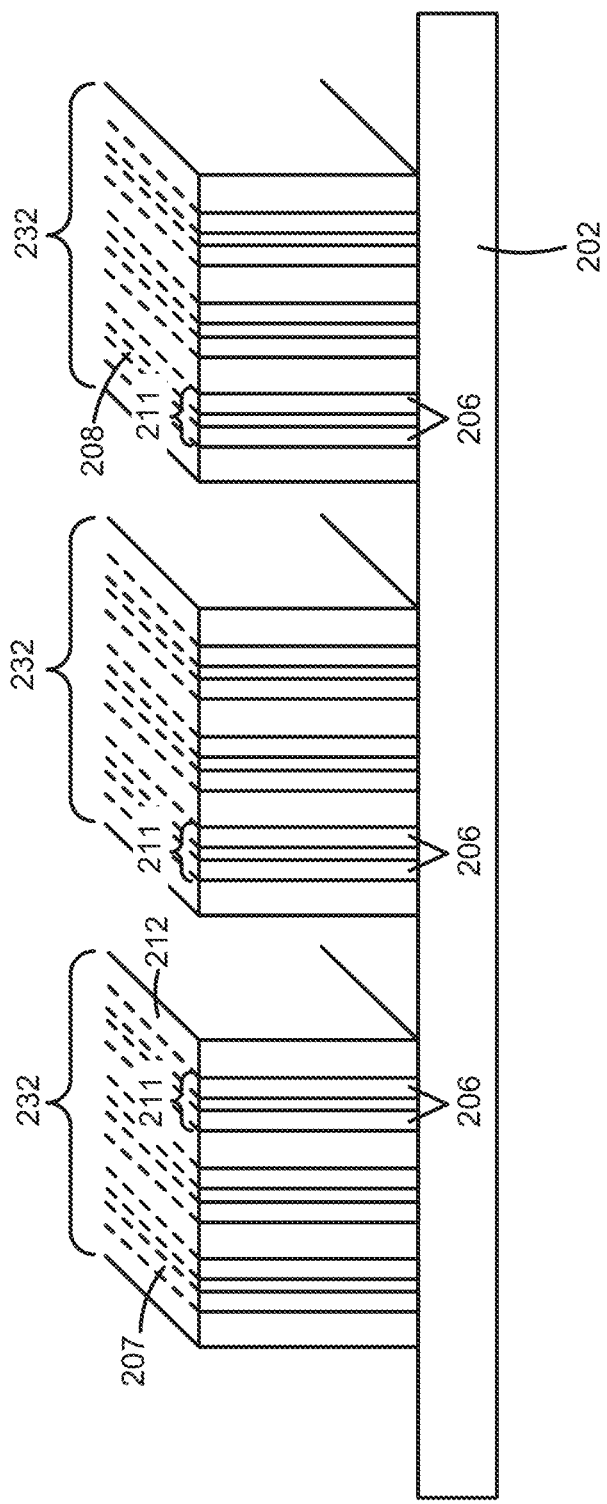
FIG. 15 illustrates the placement of multiple chips on a substrate according to an embodiment.

FIG. 15 illustrates the placement of multiple chips 232 on a substrate 202 according to an embodiment. Adding more chips 232 to the substrate 202 increases the number of pairs of electrode sheets, which in turn, provides more sites for attaching molecules to the exposed ends of the electrode sheets. In the example of FIG. 15, the chips 232 are mounted on the substrate 202 with space between the chips 232. The spaces between the chips 232 in some implementations can be filled with a potting material such as $SiO_2$ paste or a precursor to $SiO_2$, such as HSQ resist, which may be later planarized to reveal the top edges of the electrode sheets using, for example, CMP polishing, FIB etching, or PMMA or HSQ filling and etching back by RIE.

Although the example of FIG. 15 shows chips each having three pairs of electrode sheets 206, other implementations may include a different number of pairs of electrode sheets, such as chips having 2 to 2,000 pairs of electrode sheets. Each electrode sheet can have a thickness of 2 to 100 nm. In this regard, some implementations may include electrode sheets having a thickness of 1 to 40 nm or 5 to 15 nm, depending on design considerations such as the molecule to be analyzed.

Figure 16:
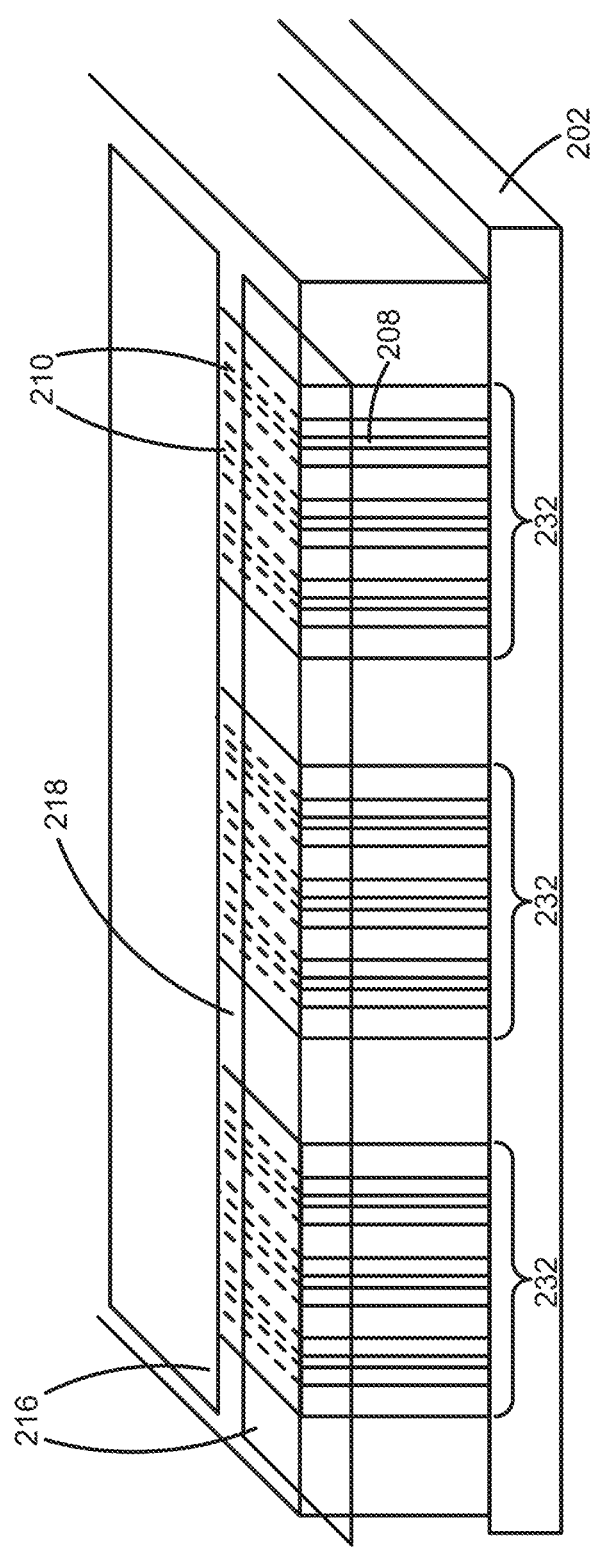
FIG. 16 illustrates the placement of a dielectric cover layer on the multiple chips of FIG. 15 according to an embodiment.

FIG. 16 illustrates the placement of a dielectric cover layer 216 on the multiple chips 232 of FIG. 15 according to an embodiment. As shown in FIG. 16, the dielectric cover layer 216 can ordinarily facilitate the attachment of only a single molecule to the exposed portions of the electrode sheets in an electrode sheet pair 206 in the gap 218. As discussed above with reference to the example of FIGS. 7A and 7B, a mask line can be deposited and then removed after the dielectric cover layer has been deposited to form the gap 218. In other implementations, the gap 218 may be formed by using a patterning process such as e-beam lithography or nano-imprinting, and etching an unmasked region to form the gap 218. In some examples, the gap can have a width between 2 to 40 nm or 5 to 15 nm to facilitate the attachment of a single molecule at each pair of electrode sheets 206.

In addition, and as discussed above with reference to block 602 in FIG. 6 and to grooves 210 in FIG. 12, an unmasked region of the inner dielectric sheets 208 can be, for example, etched by RIE, sputter etch, or a chemical etch like HF etch to form grooves 210 between the electrode sheets in the electrode sheet pairs 206.

Figure 17:
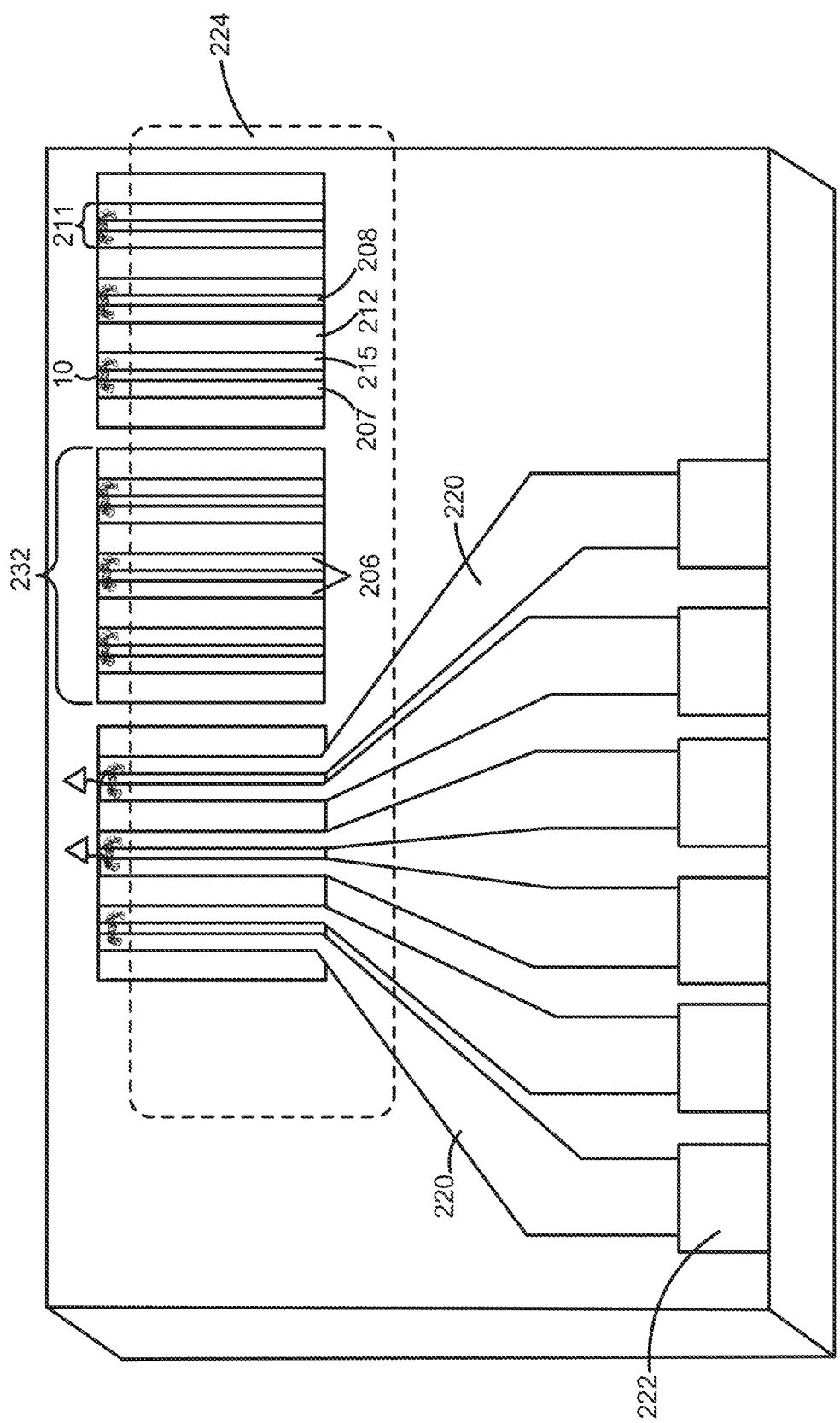
FIG. 17 is a top view of a molecular sensor with diverging lead conductors according to an embodiment.

FIG. 17 is a top view of a molecular sensor with multiple chips 232 and diverging lead conductors 220 according to an embodiment. As shown in FIG. 17, each lead conductor 220 diverges in width as the lead conductor extends away from an edge of the electrode sheet toward the contact 222. The lead conductors can be made of a conductive material such as gold for carrying a test signal from the electrode sheets. In some implementations, the thickness of the electrode sheets can be as small as only 10 nm.

The lead conductors may then fan out from a width of approximately 10 nm to a scale of micrometers to allow for soldering at the contacts 222. The contacts 222 can include a contact pad array for circuit packaging, solder bonding, or wire bonding. In addition, a dielectric cover layer 224 is deposited so that only an end portion of the electrode sheets are exposed for attaching a single molecule to each pair of electrode sheets 206.

In some implementations, a gate electrode, such as the gate electrodes 126 or 127 shown in FIG. 10 discussed above may also be applied to the molecular sensor to improve the accuracy of readings from the pairs of electrode sheets 206 by imposing an electric field to regulate the charge carriers between the first electrode sheet 207 and the second electrode sheet 215, which serve as source and drain electrodes.

Figure 18:
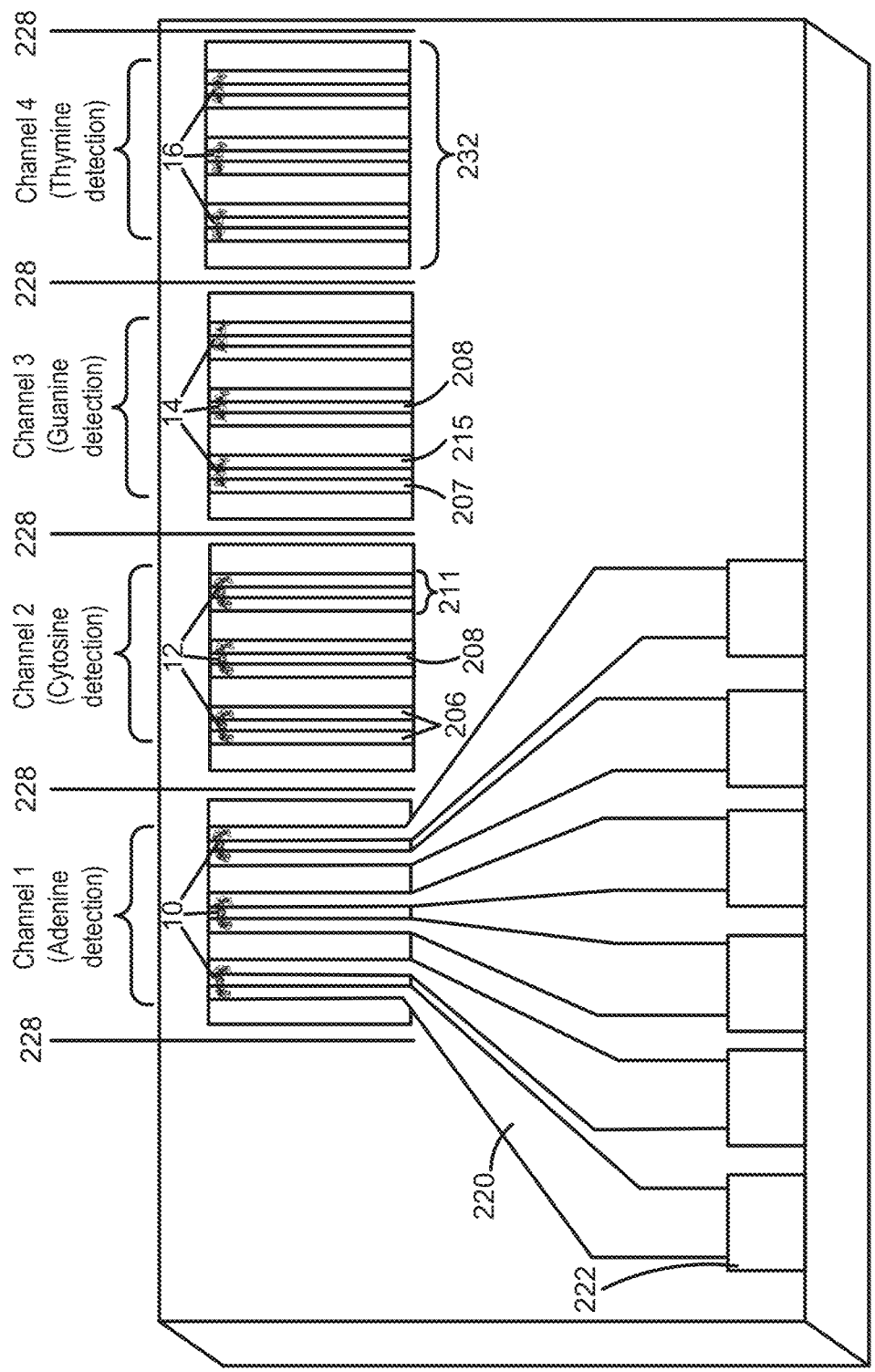
FIG. 18 is a top view of a molecular sensor with channels for introducing a fluid to pairs of electrode sheets according to an embodiment.

FIG. 18 is a top view of a molecular sensor with channels for introducing a fluid to pairs of electrode sheets according to an embodiment. In the example of FIG. 18, each chip 232 provides a separate channel with a group of pairs of electrode sheets 206, separated by a wall 228. A fluid such as a gas or liquid containing the molecules to be tested can then be introduced into the channel so that multiple pairs of electrode sheets can be used to test the molecules in the fluid. In FIG. 18, each channel is loaded with a fluid containing a different DNA nucleobase for detection via the pairs of electrode sheets 206 in the channel.

The arrangement shown in FIG. 18 can ordinarily allow for error correction or compensation by loading the same fluid to be tested (e.g., a fluid with molecules 10, 12, 14, or 16 in FIG. 18) across multiple pairs of electrode sheets 206 and using the different measurements for the different pairs of electrode sheets to average out any error and/or eliminate a measurement that deviates by more than a threshold. Although three pairs of electrode sheets are shown per channel in the example of FIG. 18, a different number of pairs can be used in different implementations, such as ten or twenty pairs of electrode sheets per channel.

In some implementations, the arrangement shown in FIG. 18 can include one or more dielectric cover layers similar to the dielectric cover layer 124 in FIG. 9 discussed above. The dielectric cover layer or layers can be deposited at an angle to or perpendicular to the electrode sheets on the surface of the chips 232 to expose only a narrow gap portion of the electrode sheets for molecular sensing.

The molecular sensor devices and fabrication methods discussed above provide numerous unique advantages that are not provided by previous molecular sensors and fabrication methods. For example, the molecular sensors disclosed above do not require nano-fabrication, positioning, and adhesion of conductive islands. Conventional molecular sensors typically include a pair of thin film electrodes facing each other in a horizontally linear configuration, with a conductive island (e.g., a gold island of 3 to 10 nm) that is transported and placed at a specific location on each electrode, or nano-pattern fabricated on each electrode. The size, adhesion strength, and positioning of such conductive islands can critically affect the performance, reliability, and yield of such conventional molecular sensors, especially in the case of genome sequencing. In some cases, the conductive islands may even fall off of the electrodes.

In contrast, the molecular sensors disclosed above do not require nano-fabrication, adhesion, or precise positioning of conductive islands. As a result, the problems associated with the variability of conductive island size, positioning, and adhesion strength are generally avoided.

As another example advantage, the arrangement of electrode sheets discussed above ordinarily allows for a much higher electrical conductance as compared to previous thin film sensor devices. This higher electrical conductance can provide an improved signal-to-noise ratio.

As yet another advantage, the disclosed processes and molecular sensors provide better control of the size of the exposed area for attachment of a molecule on the electrodes themselves. As discussed above, the use of cover layers can accurately control the size of the location for molecule attachment, which can help ensure that only a single molecule attaches to the exposed area. The foregoing processes also provide a more accurate control of the dielectric layer thickness between the electrodes, which can facilitate a higher device yield.

As yet another advantage, the fabrication processes disclosed above provide an easier and lower cost over conventional fabrication processes for molecular sensors. The multilayer deposition and planarization processes discussed above can also allow for fabrication of thousands or more massively parallel device arrays.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the present disclosure. The described embodiments are to be considered in all respects only as illustrative and not restrictive, and the scope of the disclosure is therefore indicated by the following claims rather than by the foregoing description. All changes which come within the meaning and range of equivalency of the claims are to be embraced within their scope.

What is claimed is:

1. A structure usable in a molecular sensor device, comprising:
   a substrate defining a substrate plane;
   a plurality of pairs of electrode sheets above or below the substrate at an angle to the substrate plane;
   an inner dielectric sheet between each electrode sheet in each pair of electrode sheets, wherein each inner dielectric sheet comprises a groove on an exposed end portion of the inner dielectric sheet; and
   an outer dielectric sheet between each pair of electrode sheets,
   wherein each electrode sheet is at least 1,000 μm tall,
   wherein an aspect ratio of height to thickness of each electrode sheet is at least 10,000,
   wherein each inner dielectric sheet has a first thickness, and wherein each outer dielectric sheet has a second thickness at least one order of magnitude greater than the first thickness.

2. The structure of claim 1, further comprising a dielectric cover layer covering an end portion of the plurality of pairs opposite the substrate, the dielectric cover layer defining a gap exposing a portion of the plurality of pairs.

3. The structure of claim 2, wherein the gap defined by the dielectric cover layer is between approximately 2 to 40 nanometers wide.

4. The structure of claim 1, wherein an exposed edge of each electrode sheet in the plurality of pairs opposite the substrate has been roughened.

5. The structure of claim 1, further comprising:
   a plurality of lead conductors, each lead conductor of the plurality of lead conductors extending from an electrode sheet of the plurality of pairs; and
   a plurality of contacts, each contact of the plurality of contacts in electrical communication with a lead conductor of the plurality of lead conductors; and
   wherein each lead conductor of the plurality of lead conductors diverges in width from an edge of the electrode sheet to the contact.

6. The structure of claim 1, further comprising a gate electrode parallel to the substrate plane and perpendicular to an electrode plane defined by an electrode sheet in the plurality of pairs.

7. The structure of claim 1, further comprising a plurality of channels, each channel of the plurality of channels arranged to introduce a fluid to exposed portions of at least two pairs of electrode sheets of the plurality of pairs.

8. The structure of claim 1 wherein each electrode sheet in a pair of electrode sheets is electrically connected to a current source to form an electrical circuit, and wherein a molecular sensing device comprising said electrical circuit detects a molecule when the molecule to be detected connects to both electrode sheets of the circuit to form a bridge between the electrode sheets with current passing through the molecule, said molecule comprising at least one of a DNA molecule, an antibody molecule, and a protein molecule.

9. The structure of claim 1, wherein the first thickness is at most 50 nanometers and the second thickness is at least 0.5 micrometers.

10. The structure of claim 9, further comprising a dielectric cover layer covering an end portion of the plurality of pairs opposite the substrate, the dielectric cover layer defining a gap exposing a portion of the plurality of pairs.

11. The structure of claim 10, wherein the gap defined by the dielectric cover layer is between approximately 2 to 40 nanometers wide.

12. The structure of claim 9, wherein an exposed edge of each electrode sheet in the plurality of pairs opposite the substrate has been roughened.

13. The structure of claim 9, further comprising:
   a plurality of lead conductors, each lead conductor of the plurality of lead conductors extending from an electrode sheet of the plurality of pairs; and
   a plurality of contacts, each contact of the plurality of contacts in electrical communication with a lead conductor of the plurality of lead conductors; and
   wherein each lead conductor of the plurality of lead conductors diverges in width from an edge of the electrode sheet to the contact.

14. The structure of claim 9, further comprising a gate electrode parallel to the substrate plane and perpendicular to an electrode plane defined by an electrode sheet in the plurality of pairs.

15. The structure of claim 9, further comprising a plurality of channels, each channel of the plurality of channels arranged to introduce a fluid to exposed portions of at least two pairs of electrode sheets of the plurality of pairs.

16. The structure of claim 9, wherein each electrode sheet in a pair of electrode sheets is electrically connected to a current source to form an electrical circuit, and wherein a molecular sensing device comprising said electrical circuit detects a molecule when the molecule to be detected connects to both electrode sheets of the circuit to form a bridge between the electrode sheets with current passing through the molecule, said molecule comprising at least one of a DNA molecule, an antibody molecule, and a protein molecule.

17. The structure of claim 1, wherein the first thickness is between 1 and 40 nanometers, and the second thickness is between 50 and 2,000 nanometers.

18. The structure of claim 1, further comprising an adhesion enhancing layer between each inner dielectric sheet and electrode, wherein each adhesion enhancing layer is between 1 and 5 nanometers thick, and wherein each adhesion enhancing layer comprises one of: Ti, Cr, Al, Zr, Mo, Nb, Ta, or Hf.

* * * * *